US009896672B2

(12) United States Patent
Jin et al.

(10) Patent No.: US 9,896,672 B2
(45) Date of Patent: *Feb. 20, 2018

(54) COMPOSITION AND FORMULATION COMPRISING RECOMBINANT HUMAN IDURONATE-2-SULFATASE AND PREPARATION METHOD THEREOF

(71) Applicants: GREEN CROSS CORPORATION, Yongin-si, Gyeonggi-do (KR); MediGeneBio Corporation, Yongin-si, Gyeonggi-do (KR)

(72) Inventors: Thong-Gyu Jin, Seoul (KR); Yo Kyung Chung, Yongin-si (KR); Sang Hoon Paik, Yongin-si (KR); Yoo Chang Park, Yongin-si (KR); Jinwook Seo, Yongin-si (KR); Yong Woon Choi, Yongin-si (KR); Jong Mun Son, Yongin-si (KR); Yong-Chul Kim, Yongin-si (KR)

(73) Assignees: GREEN CROSS CORPORATION, Yongin-Si (KR); MediGeneBio Corporation, Yongin-Si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/184,406

(22) Filed: Jun. 16, 2016

(65) Prior Publication Data
US 2016/0326504 A1 Nov. 10, 2016

Related U.S. Application Data

(63) Continuation of application No. 14/976,073, filed on Dec. 21, 2015, which is a continuation-in-part of application No. 14/809,856, filed on Jul. 27, 2015, now Pat. No. 9,249,397, which is a continuation of application No. 14/128,918, filed as application No. PCT/KR2012/004734 on Jun. 15, 2012, now Pat. No. 9,206,402.

(60) Provisional application No. 61/500,994, filed on Jun. 24, 2011.

(51) Int. Cl.
A61K 38/46 (2006.01)
C12N 9/16 (2006.01)
A61K 9/00 (2006.01)
A61K 47/02 (2006.01)
A61K 47/26 (2006.01)

(52) U.S. Cl.
CPC .............. *C12N 9/16* (2013.01); *A61K 9/0019* (2013.01); *A61K 38/465* (2013.01); *A61K 47/02* (2013.01); *A61K 47/26* (2013.01); *C12Y 301/06013* (2013.01)

(58) Field of Classification Search
CPC ................. C12N 9/16; A61K 38/465
USPC ...................................................... 424/94.6
See application file for complete search history.

(56) References Cited

U.S. PATENT DOCUMENTS

| | | | |
|---|---|---|---|
| 5,932,211 A | 8/1999 | Wilson et al. | |
| 6,096,555 A | 8/2000 | Hermentin et al. | |
| 6,153,188 A | 11/2000 | Wilson et al. | |
| 6,506,598 B1 | 1/2003 | Andersen et al. | |
| 6,890,736 B1 | 5/2005 | Reddy et al. | |
| 7,083,793 B2 | 8/2006 | Fraser | |
| 7,282,209 B2 | 10/2007 | Fraser | |
| 7,285,398 B2 | 10/2007 | Fraser | |
| 7,323,553 B2 | 1/2008 | Fahrner et al. | |
| 7,368,531 B2 | 5/2008 | Rosen et al. | |
| 7,541,164 B2 | 6/2009 | Schilling et al. | |
| 7,691,611 B2 | 4/2010 | Weber et al. | |
| 8,128,925 B2 | 3/2012 | Vellard et al. | |
| 8,198,084 B2 | 6/2012 | Gorfien et al. | |
| 8,227,212 B2 | 7/2012 | von Figura et al. | |
| 9,051,556 B2 | 6/2015 | Nichols | |
| 9,206,402 B2* | 12/2015 | Jin ..................... | A61K 38/465 |
| 9,249,397 B2* | 2/2016 | Jin ..................... | A61K 38/465 |
| 2002/0106358 A1 | 8/2002 | Hopwood et al. | |
| 2004/0229250 A1 | 11/2004 | Figura et al. | |
| 2006/0148074 A1 | 7/2006 | Gorfien et al. | |
| 2011/0318323 A1 | 12/2011 | Zhu et al. | |
| 2013/0028881 A1 | 1/2013 | von Figura et al. | |
| 2014/0004097 A1 | 1/2014 | Zhang et al. | |
| 2014/0004593 A1 | 1/2014 | Boldog et al. | |

FOREIGN PATENT DOCUMENTS

| | | |
|---|---|---|
| EP | 2330204 A1 | 6/2011 |
| JP | H10500939 A | 1/1998 |
| JP | 2002017376 A | 1/2002 |
| KR | 101158673 B1 | 7/2012 |
| WO | 0050443 A2 | 8/2000 |

(Continued)

OTHER PUBLICATIONS

State Intellectual Property Office of People's Republic of China, Communication dated Aug. 27, 2014, issued in corresponding Chinese application No. 201280030629.X.

Sohn et al. "Safety and efficacy of enzyme replacement therapy with idursulfase beta in children aged younger than 6 years with Hunter syndrome", Molecular Genetics and Metabolism Aug. 6, 2014; pp. 1-5.

Sohn et al. "Phase I/II clinical trial of enzyme replacement therapy with idursulfase beta in patients with mucopolysaccharidosis II (Hunter Syndrome)", Orphanet Journal of Rare Diseases, Mar. 18, 2013, 8:42. pp. 1-8.

Muenzer, Joseph et al., "A phase II/III clinical study of enzyme replacement therapy with idursulfase in mucopolysaccharidosis II (Hunter syndrome)", Genetics in Medicine, vol. 8, No. 8, pp. 465-473.

(Continued)

*Primary Examiner* — Tekchand Saidha
(74) *Attorney, Agent, or Firm* — Sughrue Mion, PLLC

(57) ABSTRACT

A composition comprising recombinant iduronate-2-sulfatase (IDS) and a method for producing a purified recombinant IDS are provided. The glycosylation pattern and formylglycine content of the IDS composition are different from those of ELAPRASE® and have superior pharmaceutical efficacy and are safer than the conventional agent and thus can be effectively used for the therapy of Hunter syndrome.

27 Claims, 27 Drawing Sheets

(56) References Cited

FOREIGN PATENT DOCUMENTS

| WO | 0118022 A1 | 3/2001 |
|---|---|---|
| WO | 0160991 A2 | 8/2001 |
| WO | 0177137 A1 | 10/2001 |
| WO | 02059327 A2 | 8/2002 |
| WO | 02098455 A2 | 12/2002 |
| WO | 2004072275 A2 | 8/2004 |
| WO | 2005113765 A2 | 12/2005 |
| WO | 2011044542 A1 | 4/2011 |
| WO | 0155411 A2 | 8/2011 |
| WO | 0170804 A1 | 9/2011 |
| WO | 2011163649 A2 | 12/2011 |
| WO | 2012/101671 A1 | 8/2012 |
| WO | 2012177020 A2 | 12/2012 |

OTHER PUBLICATIONS

Muenzer, J. et al. 'A Phase I/II Clinical Trial of Enzyme Replacement Therapy in Mucopolysaccharidosis II (Hunter Syndrome)', Molecular Genetics and Metabolism, 2007, vol. 90 pp. 329-337.
Iduronate 2-sulfatase isoform a precursor [Homo sapiens], NCBI Reference Sequence: NP_000193.1, May 14, 2011, 3 pages total.
Fraldi A et al.., "SUMF1 enhances sulfatase activities in vivo in five sulfatase deficiencies", Biochemical Journal, Portland Press Ltd., GB, vol. 403, No. 2, Apr. 15, 2007, pp. 305-312, XP002601852, ISSN: 0264-6021.
European Patent Office, communication dated Nov. 20, 2014 from The European Patent Office in counterpart European Patent Application No. 12803297.6.
Chung et al., "A biochemical and physicochemical comparison of two recombinant enzymes used for enzyme replacement therapies of hunter syndrome", Glycoconjugate Journal, vol. 31, No. 4, Apr. 30, 2014, pp. 309-315, XP55149968, ISSN: 0282-0080.
Chung et al. "A biochemical and physicochemical comparison of two recombinant enzymes used for enzyme replacement therapies of hunter syndrome", Glycoconj J (2014) 31: pp. 309-315.
Cho et al. "Impact of Enzyme Replacement Therapy on Linear Growth in Korean Patients with Mucopolysaccharidosis Type II (Hunter Syndrome)", J Korean Med Sci 2014; 29: pp. 254-260.
Bielicki, "Recombinant human iduronate-2-sulphatase: correction of mucopolysaccharidosis-type II fibroblasts and characterization of purified enzyme", Biochemial Jourbal, vol. 289, Jan. 1, 1993, pp. 241-246, XP055081180, GB ISSN: 0264-6021.
Australian Patent Office, communication dated Apr. 1, 2015 in counterpart application No. 2012274215.
P.J. Wilson et al. "Hunter syndrome: Isolation of an iduronate-2-sulfatase cDNA clone and analysis of patient DNA" Proc. Natl. Acad. Sci USA, vol. 87; 8531-8535 (Nov. 1990).
Bernhard Schmidt et al. "A Novel Amino Acid Modification in Sulfatases That Is Defective in Multiple Sulfatase Deficiency" Cell, vol. 82, pp. 271-278, Jul. 28, 1995.
Lorne A. Clarke "Idursulfase for the treatment of mucopolysaccharidosis II" Expert Opinion on Pharmacology, 9(2); 311-317 (2008) Drug Evaluation.
Thomas Dierks et al. "Multiple Sulfatase Deficiency Is Caused by mutations in the Gene Encoding the Human Cα-Formylglycine Generating Enzyme" Cell, vol. 113, pp. 435-444; May 16, 2003.
European Patent Office; Communication dated Jan. 23, 2017, in counterpart European Application No. 12803297.6.
Maria P. Cosma et al. "The Multiple Sulfatase Deficiency Gene Encodes an Essential and Limiting Factor for the Activity of Sulfatases" Cell, vol. 113, May 16, 2003; pp. 445-456.
United States Patent and Trademark Office; Petition for Inter Partes review of U.S. Pat. No. 9,051,556 Under 35 U.S.C. §§ 311-319 and 37 C.F.R. §§ 42.1-80, 42.100 et seq.
United States Patent and Trademark Office; Inter Partes review of U.S. Pat. No. 9,051,556; Case OPR No. 2016-00258.
Indonesian Patent Office: Communication dated Nov. 14, 2016 in counterpart application No. P-00201400111.
Burrow et al. "Review of the use of idursulfase in the treatment of mucopolysaccharidosis II" Biologics: Targets and Therapy 2008: 2(2); pp. 311-320.
Bielicki, J. et al., 1990, Biochem. J., 271,75-86 "Human liver iduronate-2-sulphatase. Purification, characterization and catalytic properties".
Final Written Decision before the United States Patent and Trademark Office and the Patent Trials and Appeal Board Case No. IPR2016-00258; entered Mar. 22, 2017.
Abdella et al., A new cleavable reagent for cross-linking and reversible immobilization of proteins. Biochem Biophys Res Commun. Apr. 13, 1979;87(3):734-42.
Benjdia et al., First evidences for a third sulfatase maturation system in prokaryotes from E. coli asIB and ydeM deletion mutants. FEBS Lett. Mar. 6, 2007;581(5):1009-14.
Bielicki et al., Expression, purification and characterization of recombinant human N-acetylgalactosamine-6-sulphatase. Biochem J. Oct. 1, 1995;311 (Pt 1):333-9.
Burgess, R. Protein Purification, Proteomics of the Nervous System, 1-18 (2005).
Chica et al., Semi-rational approaches to engineering enzyme activity: combining the benefits of directed evolution and rational design. Curr Opin Biotechnol. Aug. 2005;16(4):378-84.
Database EMBL, Database Accession No. AAAB01008987 (Jul. 24, 2002).
Database EMBL, Database Accession No. AAB88402 (May 23, 2001).
Database EMBL, Database Accession No. AAY95971 (Dec. 5, 2000).
Database EMBL, Database Accession No. ABB62912 (Mar. 26, 2002).
Database EMBL, Database Accession No. AK076022 (Dec. 13, 2002).
Database EMBL, Database Accession No. BD551115 (Sep. 18, 2002).
Database EMBL, Database Accession No. P95060 (May 1, 1997).
Database EMBL, Database Accession No. Q7V5N5 (Oct. 1, 2003).
Database EMBL, Database Accession No. Q88HK3 (Jun. 1, 2003).
Database EMBL, Database Accession No. Q8FTJ8 (Mar. 1, 2003).
Database EMBL, Database Accession No. Q92WL9 (Dec. 1, 2001).
Database EMBL, Database Accession No. Q93PA2 (Dec. 1, 2001).
Database EMBL, Database Accession No. Q98BQ8 (Oct. 1, 2001).
Database EMBL, Database Accession No. Q9A921 (Jun. 1, 2001).
Database EMBL, Database Accession No. Q9F3C7 (Mar. 1, 2001).
Dierks et al., Conversion of cysteine to formylglycine: a protein modification in the endoplasmic reticulum. Proc Natl Acad Sci U S A. Oct. 28, 1997;94(22):11963-8.
Dierks et al., Sequence determinants directing conversion of cysteine to formylglycine in eukaryotic sulfatases. EMBO J. Apr. 15, 1999;18(8):2084-91.
Eto et al., Multiple sulfatase deficiency (mucosulfatidosis): impaired degradation of labeled sulfated compounds in cultured skin fibroblasts in vivo. Eur J Pediatr. Oct. 1980;135(1):85-9.
Fang et al., Post-translational formylglycine modification of bacterial sulfatases by the radical S-adenosylmethionine protein AtsB. J Biol Chem. Apr. 9, 2004;279(15)1 4570-8.
Ferrante et al., Molecular and biochemical characterisation of a novel sulphatase gene: Arylsulfatase G (ARSG). Eur J Hum Genet. Dec. 2002;10(12):813-8.
Fey et al., Characterization of posttranslational formylglycine formation by luminal components of the endoplasmic reticulum. J Biol Chem. Dec. 14, 2001;276(50):47021-8.
GenBank Accession No. AJ131525 (Apr. 14, 1999).
International Search Report and Written Opinion for PCT/US13/48561, dated Dec. 12, 2013.
International Search Report and Written Opinion for PCT/US13/48571, dated Dec. 12, 2013.
International Search Report and Written Opinion for PCT/US13/48601, dated Dec. 3, 2013.
Juengst, E. What next for human gene therapy? Gene transfer often has multiple and unpredictable effects on cells. BMJ. Jun. 28, 2003;326(7404)1 410-1.

(56) References Cited

OTHER PUBLICATIONS

Knaust et al., Residues critical for formylglycine formation and/or catalytic activity of arylsulfatase A. Biochemistry. Oct. 6, 1998;37(40):13941-6.

Landgrebe et al., The human SUMF1 gene, required for post-translational sulfatase modification, defines a new gene family which is conserved from pro- to eukaryotes. Gene. Oct. 16, 2003;316:47-56.

Merriam-Webster online dictionary definition of "exogenous", obtained from <www.merriam-webster.com/dictionary/exogenous>, accessed on Aug. 4, 2010.

Merriam-Webster online dictionary definition of "exogenous", obtained from <www.merriam-webster.com/dictionary/exogenous>, accessed on Dec. 18, 2009.

Morimoto-Tomita et al., Cloning and characterization of two extracellular heparin-degrading endosulfatases in mice and humans. J Biol Chem. Dec. 20, 2002;277(51):49175-85.

Plasmid Vectors, obtained from WININ.mfa.od.ua/page275.htm, last viewed on May 9, 2011 (2 pages).

Rivera-Colon et al., The structure of human GALNS reveals the molecular basis for mucopolysaccharidosis IV A. J Mol Biol. Nov. 9, 2012;423(5):736-51.

Rommerskirch et al., Multiple sulfatase deficiency: catalytically inactive sulfatases are expressed from retrovirally introduced sulfatase cDNAs. Proc Natl Acad Sci U S A. Apr. 1, 1992;89(7):2561-5.

Sang, H. Prospects for transgenesis in the chick. Mech Dev. Sep. 2004;121 (9):1179-86.

Schirmer et al., Computational analysis of bacterial sulfatases and their modifying enzymes. Chem Biol. Aug. 1998;5(8):R181-6.

Sen et al., Developments in directed evolution for improving enzyme functions. Appl Biochem Biotechnol. Dec. 2007;143(3):212-23.

Szameit et al., The iron sulfur protein AtsB is required for post-translational formation of formylglycine in the Klebsiella sulfatase. J Biol Chem. May 28, 1999;274(22):15375-81.

Tomatsu et al., Morquio disease: isolation, characterization and expression of full-length cDNA for human N-acetylgalactosamine-6-sulfate sulfatase. Biochem Biophys Res Commun. Dec. 16, 1991;181(2):677-83.

U.S. Department of Health and Human Services, Food and Drug Administration, Guidance for Industry, Scientific Consideration in Demonstrating Biosimilarity to a Reference Product, 1-22 (Feb. 2012).

Wraith et al., The clinical phenotype of two patients with a complete deletion of the iduronate-2-sulphatase gene (mucopolysaccharidosis II—Hunter syndrome). Hum Genet. Jun. 1991;87(2):205-6.

* cited by examiner

Lane M: Protein size marker
Lane 1: glycosylated IDS
Lane 2: IDS treated with PNGase
Eane 3: deglycosylated IDS

FIG. 6

```
        10         20         30         40         50
SETQANSTTD ALNVLLIIVD DLRPSLGCYG DKLVRSPNID QLASHSLLFQ
        60         70         80         90        100
NAFAQQAVCA PSRVSFLTGR RPDTTRLYDF NSYWRVHAGN FSTIPQYFKE
       110        120        130        140        150
NGYVTMSVGK VFHPGISSNH TDDSPYSWSF PPYHPSSEKY ENTKTCRGPD
       160        170        180        190        200
GELHANLLCP VDVLDVPEGT LPDKQSTEQA IQLLEKMKTS ASPFFLAVGY
       210        220        230        240        250
HKPHIPFRYP KEFQKLYPLE NITLAPDPEV PDGLPPVAYN PWMDIRQRED
       260        270        280        290        300
VQALNISVPY GPIPVDFQRK IRQSYFASVS YLDTQVGRLL SALDDLQLAN
       310        320        330        340        350
STIIAPTSDH GWALGEHGEW AKYSNFDVAT HVPLIFYVPG RTASLPEAGE
       360        370        380        390        400
KLFPYLDPFD SASQLMEPGR QSMDLVELVS LFPTLAGLAG LQVPPRCPVP
       410        420        430        440        450
SFHVELCREG KNLLKHFRFR DLEEDPYLPG NPRELIAYSQ YPRPSDIPQW
       460        470        480        490        500
NSDKPSLKDI KIMGYSIRTI DYRYTVWVGF NPDEFLANFS DIHAGELYFV
       510        520        530
DSDPLQDHNM YNDSQGGDLF QLLMP  (SEQ ID NO: 1)
```

FIG. 10

| | | | | | | | | | |
|---|---|---|---|---|---|---|---|---|---|
| SETQR | 10 NSTTD | ALNNL | 20 LIIUD | DLRPS | 30 LCNYG | DKLUR | SPNID | 40 | QLASH | SLLPQ | 50 | MAPAQ | QNUCR | 60 |

(illegible sequence table — SEQ ID NO: 1)

Lane 1, 8: Molecular size marker
Lane 2: IDS
Lane 3: IDS treated with PNGase F
Lane 4: IDS treated with Endo H
Lane 5: IDS treated with O-glycosidase
Lane 6: IDS treated with Sialidase
Lane 7: IDS treated with PNGase F and O-glycosidase Lane M: size marker
Lane 1: a loaded sample for cation exchange chromatography
Lane 2: an eluate of cation exchange chromatography
Lane 3: a regeneration solution after cation exchange chromatography

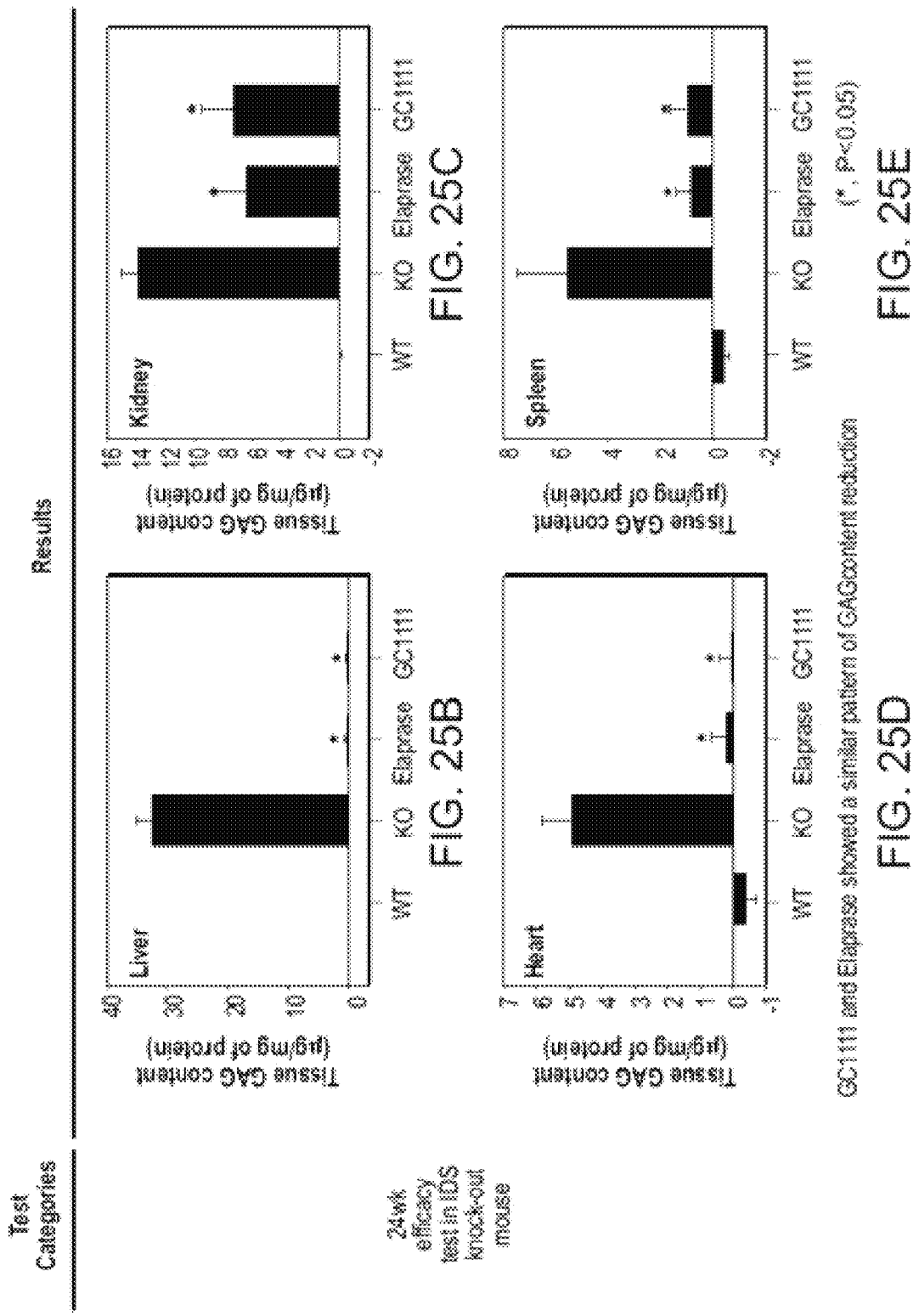

COMPOSITION AND FORMULATION COMPRISING RECOMBINANT HUMAN IDURONATE-2-SULFATASE AND PREPARATION METHOD THEREOF

CROSS REFERENCE TO RELATED APPLICATIONS

This application is a continuation of Ser. No. 14/976,073 filed Dec. 21, 2015 (pending), which is a continuation-in-part of application Ser. No. 14/809,856 filed Jul. 27, 2015 (issued as U.S. Pat. No. 9,249,397), which is a continuation of application Ser. No. 14/128,918 filed Dec. 23, 2013 (issued as U.S. Pat. No. 9,206,402), which is a National Stage of International Application No. PCT/KR2012/004734 filed Jun. 15, 2012, claiming priority based on Korean Patent Application No. 10-2012-0012718 filed Feb. 8, 2012 and U.S. Provisional Patent Application No. 61/500,994 filed Jun. 24, 2011, the contents of all of which are incorporated herein by reference in their entirety.

TECHNICAL FIELD

The present invention relates to a composition for the treatment of Hunter syndrome, comprising recombinant human iduronate-2-sulfatase (hereinafter referred to as "IDS"), a formulation comprising the same, and a method for preparing the same.

More particularly, the composition for the treatment of Hunter syndrome in accordance with the present invention comprises as an active ingredient IDS having an amino acid sequence represented by SEQ ID NO: 1, wherein cysteine residue at position 59 in the IDS amino acid sequence of SEQ ID NO: 1 is converted to formylglycine (FGly: 2-amino-3-oxopropionic acid) at a molar ratio of 65% or higher, preferably at a molar ratio of 75% or higher, and more preferably at a molar ratio of 80% or higher. The IDS peptide of SEQ ID NO: 1 wherein the amino acid residue at position 59 is formylglycine is identified as SEQ ID NO: 9. In addition, the IDS contained in the composition for the treatment of Hunter syndrome contains mannose-6-phosphate in an amount of 2.0 to 4.0 moles per mole of IDS, preferably in an amount of from 2.3 to 3.5 moles, and more preferably in an amount of from 2.5 to 3.0 moles.

The method for preparing the composition for the treatment of Hunter syndrome in accordance with the present invention comprises:

(1) culturing a recombinant cell line transfected with a gene encoding IDS represented by SEQ ID NO: 1 and obtaining the culture; and (2) purifying the culture through anion exchange chromatography, hydrophobic chromatography, cation exchange chromatography, and affinity chromatography, characterized in that the recombinant cell line is cultured in the presence of a hydrolysate and the cation exchange chromatography may be performed using an eluting buffer with a pH of 4.0 to 6.0.

In an exemplary embodiment, the cation exchange chromatography may be performed at a pH of 5.3±0.2.

Having advantages over conventional products in terms of safety and pharmaceutical efficacy, the therapeutic composition comprising IDS and the formulation comprising the same can be effectively used to treat Hunter syndrome.

BACKGROUND ART

Hunter syndrome or mucosaccharidosis type II is a lysosomal storage disease (LSD) in which mucopolysaccharides, also known as glycosaminoglycans (GAG), are not broken down correctly and build up in the body due to a deficiency of IDS. As GAG continues to buildup throughout the cells of the body, various signs of Hunter syndrome become more visible. Physical manifestations for some people with Hunter syndrome include distinct facial features and a large head. Representative among the symptoms of Hunter syndrome are an enlarged abdomen due to hepatomegaly or splenomegaly, deafness, valvular heart disease, obstructive airway disease and sleep apnea. Also, major joints may be affected by Hunter syndrome, leading to joint stiffness and limited motion. In some cases of Hunter syndrome, central nervous system involvement leads to developmental delays and nervous system problems. Hunter syndrome is a known to occur at a rate of 1 in 162,000 and is a genetic disorder in the form of chromosome X-linked recessive and so given the great suffering to the family as well as the patient.

Various trials have been carried out thus regarding the treatment of Hunter syndrome, including bone marrow graft, enzyme replacement, and gene therapy. While bone marrow graft is able to stop most of the symptoms, it is difficult to find an HLA (human leukocyte antigen) match for all patients. Further, a bone marrow graft is a major surgical operation accompanied by several adverse effects, including the patient's life being put under high risk if the HLA is mismatched. Gene therapy for Hunter syndrome delivers a normal IDS gene into the body with the aid of a viral vector such as adenovirus or retrovirus or a non-viral vector. However, gene therapy remains an experimental technique, and has not been clinically applied. As for the enzyme replacement treatment for Hunter syndrome, it administers externally produced IDS and has the advantage of being simple. However, enzyme replacement must be continuously carried out, which incurs a high expense. ELAPRASE® (Shire Pharmaceuticals Group), produced using recombinant DNA technology, was approved by the FDA as an enzyme replacement treatment for Hunter syndrome. However, this drug is very expensive and suffers from the drawbacks of insufficient efficacy and safety.

As described above, although various therapies for Hunter syndrome have been developed, there is still a pressing need for a new therapy and agent that exhibits high therapeutic efficacy with high safety.

DISCLOSURE

Technical Problem

It is an object of the present invention to overcome the problems encountered in the prior art and to provide a composition for the therapy of Hunter syndrome, comprising recombinant IDS as an active ingredient, which guarantees high therapeutic efficacy and safety, as produced by improved culturing and purifying processes, and a formulation comprising the same.

It is another object of the present invention to provide a method for preparing the composition for the treatment of Hunter syndrome and the formulation comprising the same.

Technical Solution

To achieve the above object, the present invention provides a composition for the therapy of Hunter syndrome, comprising as an active ingredient a recombinant IDS having an amino acid sequence represented by SEQ ID NO: 1, wherein cysteine residue at position 59 is converted to formylglycine (FGly) at a molar ratio of 65% or higher, preferably at a molar ratio of 75% or higher, and more preferably at a molar ratio of 80% or higher.

IDS, herein also called iduronate-2-sulfatase or I2S, has a molecular size of 56 kDa when isolated and purified from the human liver, kidney or placenta (Bielicki, J. et al. (1990) *Biochem, J.*, 271: 75~86). IDS is expressed as a monomeric protein of 550 amino acids and is secreted into the medium as a mature active protein of 525 amino acids following cleavage of the 25 amino acid signal peptide. The molecular weight of IDS varies with glycosylation and was found to range from approximately 60 to 90 kDa upon treatment with endoglycosidase F, as measured by SDS-PAGE.

IDS contains two disulfide bonds and eight N-linked glycosylation sites and is produced as a glycoprotein after undergoing post-translation modification in which the N-linked glycosylation sites are occupied by complex, hybrid and high mannose type oligosaccharide chains in eukaryotes. Once secreted into the culture medium, IDS may be used as a drug after going through typical isolation and purification processes. IDS may be in the form of glycoproteins with various glycosylation patterns, depending on various factors, including, for example, IDS genetic recombination, transfection (e.g., used cell lines), culture and purification techniques.

In this invention, it is disclosed that the content of mannose-6-phosphate (M6P) and the conversion ratio of Cys-59 to FGly have a great influence on the therapeutic efficacy and safety of IDS. The presence of mannose-6-phosphate (M6P) residues allows specific binding of the enzyme to M6P receptors on the cell surface, leading to cellular internalization of the enzyme, targeting of lysosomes and subsequent catabolism of accumulated GAG. Biological activity of IDS is also dependent on a post-modification of the conserved cysteine (position 59) to formylglycine.

Unless stated otherwise, the term "IDS," as used herein, means a carbohydrate-attached IDS protein, that is, a glycosylated IDS. The IDS of the present invention preferably has an amino acid sequence of SEQ ID NO: 1, but is not limited thereto. It should be apparent to those who have ordinary knowledge in the art (hereinafter referred to as "ordinary artisan") that so long as it allows the IDS to retain the desired activity, any amino acid sequence in which mutations such as insertion, deletion and substitution occur on some amino acid residues of the amino acid sequence of SEQ ID NO: 1 falls within the scope of the present invention.

As used herein, the term "glycosylation pattern" of IDS refers to the profile of oligosaccharides bound to the eight glycosylation sites of the resulting IDS (e.g., glycosylation sites and kinds of oligosaccharides).

In one embodiment, the IDS contained in the composition for the therapy of Hunter syndrome in accordance with the present invention has the same amino acid sequence as is known (SEQ ID NO: 1), but has a different glycosylation pattern and a different conversion ratio of cysteine at position 59 to formyl glycine, as described above (refer to Examples 1-5 and 1-6).

That is, the IDS used in the composition for the therapy of Hunter syndrome according to the present invention has an amino acid sequence of SEQ ID NO: 1 with the conversion of cysteine at position 59 to formyl glycine (FGly) at a molar ratio of 65% or higher, preferably at a molar ratio of 75% or higher, and more preferably at a molar ratio of 80% or higher, whereas the conversion ratio in ELAPRASE® is approximately 50% (Genet Med 2006:8(8):465-473). Formylglycine is known to be deeply involved in the ability of IDS to degrade the substrate, that is the activity of IDS. Thus, because the composition of the present invention and the conventional agent ELAPRASE® are different, the composition and the formulation according to the present invention can exhibit higher therapeutic efficacy for Hunter syndrome than can the conventional agent ELAPRASE® because of a greater cytosine to formylglycine conversion ratio at position 59 on the amino acid sequence of IDS.

In addition, the IDS used in the composition or the formulation for the therapy of Hunter syndrome in accordance with the present invention contains mannose-6-phosphate in an amount of from 2.0 to 4.0 moles per mole of IDS, preferably in an amount of from 2.3 to 3.5 moles and more preferably in an amount of from 2.5 to 3.0 moles. M6P plays an important role in the cellular internalization of IDS and subsequent targeting to intracellular lysosomes. Thus, the formulation of the present invention comprising IDS with a high content of M6P guarantees the high performance of the receptor-mediated uptake mechanism for this enzyme and targeting to lysosomes, thereby resulting in the effective catabolism of accumulated GAG.

The formulation for the therapy of Hunter syndrome comprising IDS in accordance with the present invention can be prepared by formulating the composition of the present invention with a pharmaceutically acceptable carrier into a suitable form.

According to the recommendation from the World Health Organization (WHO), Guidelines on the Quality, Safety, and Efficacy of Biotherapeutic Protein Products Prepared by Recombinant DNA Technology, adopted by the 64$^{th}$ meeting of the WHO Expert Committee on Biological Standardization, 21-25 Oct. 2013, the level of cell-derived and plasmid-derived DNA should be not more than 10 ng per purified dose. For biological medicines used chronically over a lifetime (e.g. human insulin, erythropoietin or factor VIII), the level of host-cell proteins should be not more than 10 parts per million. (TGA Guidance 18. Australian Government, Version 1.0, August 2013)

As used herein, the term "pharmaceutically acceptable" carrier refers to a non-toxic, physiologically compatible vehicle for the active ingredient, which is suitable for ingestion by animals, without undue toxicity, incompatibility, instability, irritation, allergic response and the like.

The composition according to the present invention may be formulated with a suitable vehicle depending on the administration route taken. The formulation according to the present invention may be administered orally or parenterally but this is not limited to these. For parenteral administration, a route selected from among transdermal, intranasal, intraperitoneal, intramuscular, subcutaneous or intravenous routes may be taken.

For oral administration, the pharmaceutical composition may be formulated in combination with a suitable oral vehicle into powders, granules, tablets, pills, troches, capsules, liquids, gels, syrups, suspensions and wafers using a method known in the art. Examples of the suitable vehicle useful in the formulation include sugars such as lactose, dextrose, sucrose, sorbitol, mannitol, xylitol, erythritol and maltitol, starches such as corn starch, wheat starch, rice starch, and potato starches, celluloses such as cellulose, methyl cellulose, sodium carboxymethyl cellulose, and hydroxypropyl methyl cellulose, and fillers such as gelatin and polyvinylpyrrolidone. Optionally, the formulation may further comprise a disintegrant such as crosslinked polyvinylpyrrolidone, agar, alginic acid or sodium alginate. In addition, an anti-agglomerating agent, a lubricant, a wetting agent, a fragrant, an emulsifier, and a preservative may be further employed.

Also, the composition of the present invention may be formulated in combination with a parenteral vehicle into a parenteral dosage form such as an injectable preparation, a transdermal preparation or an intranasal inhalation using a method well known in the art. For use in injection, the formulation must be sterilized and protected from contamination with microorganisms such as bacteria and fungi. Examples of the vehicle suitable for injection may include, but are not limited to, water, ethanol, polyol (e.g., glycerol, propylene glycol, liquid polyethylene glycol, etc.), combinations thereof, and/or a vegetable oil-containing solvent or dispersion medium. More preferably, the vehicle may be an isotonic solution such as Hank's solution, a Ringer's solution, triethanol amine-containing PBS (phosphate buffered saline) or injectable sterile water, 10% ethanol, 40% propylene glycol and 5% dextrose. In order to protect the injectable preparation from microbial contamination, it may further comprise an antibacterial and antifungal agent such as paraben, chlorobutanol, phenol, sorbic acid, thimerosal, etc. Also, the injectable preparations may further comprise, in most cases, an isotonic agent such as sugar or sodium chloride. These formulations are disclosed in a document well known in the pharmaceutical field (Remington's Pharmaceutical Science, 15$^{th}$ Edition, 1975, Mack Publishing Company, Easton, Pa.). As concerns inhalation, the formulation according to the present invention may be delivered conveniently in the form of an aerosol spray from a compressed pack or sprayer using a suitable propellant, such as dichlorofluoromethane, trichlorofluoromethane, dichlorotetrafluoroethane, carbon dioxide or a suitable gas. In the case of compressed aerosol, the unit size of a dose may be determined by a valve for delivering a metered amount. For example, gelatin capsules and cartridges for use in an inhaler or insufflator can be formulated containing a powder mix of the compound and a suitable powder base such as lactose or starch for these systems.

Other suitable pharmaceutical vehicles are described in Remington's Pharmaceutical Sciences, 19$^{th}$ ed., Mack Publishing Company, Easton, Pa., 1995.

Moreover, the formulation according to the present invention may further comprise one or more buffers (e.g., saline or PBS), carbohydrates (e.g., glucose, mannose, sucrose or dextran), stabilizers (sodium hydrogen sulfite, sodium sulfite or ascorbic acid), anti-oxidants, bacteriostatics, chelating agents (e.g., EDTA or glutathione), adjuvants (e.g., aluminum hydroxide), suspending agents, thickeners and/or preservatives (benzalkonium chloride, methyl- or propyl-paraben and chlorobutanol).

Also, the composition of the present invention may be formulated into a dosage form that allows the rapid, sustained or delayed release of the active ingredient after being administered into mammals. An effective amount of the formulation thus prepared may be administered via a variety of routes including oral, transdermal, subcutaneous, intravenous and intramuscular routes. The term "effective amount," as used herein refers to an amount of IDS that allows tracing the diagnostic or therapeutic effect to take place when administered into a patient. The dose of the formulation according to the present invention may vary depending on various factors including, the route of administration, the type of subject to be treated, the type of disease to be treated, the administration route, the severity of the illness, and the patient's age, gender, weight, condition, and health state. The formulation comprising IDS according to the present invention may be used at a dose of from 0.1 to 10 mg/kg and preferably at a dose of from 0.5 to 1.0 mg/kg per dosage.

The method for preparing the therapeutic composition in accordance with the present invention comprises:

(1) culturing a recombinant cell line transfected with a gene encoding IDS represented by SEQ ID NO: 1 and obtaining the culture; and (2) purifying the culture through anion exchange chromatography, hydrophobic chromatography, cation exchange chromatography, and affinity chromatography, wherein, the recombinant cell line is cultured in the presence of a hydrolysate and the cation exchange chromatography is performed using an eluting buffer with a pH of 4.0 to 6.0.

More particularly, the method for preparing the therapeutic composition in accordance with the present invention comprises:

(1) transfecting a host cell with an expression vector carrying a IDS gene to obtain a recombinant cell line;

(2) culturing the recombinant cell line in the presence of a hydrolysate in a serum-free medium and obtaining the culture;

(3) purifying IDS from the culture through anion exchange chromatography, hydrophobic chromatography, cation exchange chromatography and affinity chromatography, said cation exchange chromatography being performed using an eluting buffer ranging in a pH from 4.0 to 6.0;

(4) combining the purified IDS with a pharmaceutically acceptable carrier.

In an exemplary embodiment, an eluting buffer used in the cation exchange chromatography may have a pH of 5.3±0.2.

In the method, step (1) is directed to establishing a recombinant cell line by introducing an expression vector carrying an IDS gene into a host cell. The amino acid sequence of IDS and a gene encoding IDS are known in the art. A gene that codes for the IDS having the amino acid sequence of SEQ ID NO: 1 is preferred, but is not provided as a limiting example. If an amino acid sequence retains the activity of IDS sought to be brought about by the purpose of the present invention, although mutated by insertion, deletion and/or substitution of some amino acid residues on the amino acid sequence of SEQ ID NO: 1, its gene may be used in the present invention. The expression vector carrying the gene may be constructed using a typical method known in the art. In addition, the expression vector may contain a marker gene which allows the introduction of the gene to be identified. Examples of the marker gene include a dihydrofolate reductase gene (dhfr), but are not limited thereto. Preferable is a pJK-dhfr-Or2-IDS vector (FIG. 2).

The host cells available for step (1) may be animal cells and their examples include, but are not limited to, Chinese hamster ovary (CHO) cells, human embryonic kidney (HEK) cells, baby hamster kidney (BHK) cells, monkey kidney cell 7 (COS7), and NSO cells, with a preference for CHO cells. CHO cell lines are one of the most widely used in the production of biomedical products thanks to their high cell growth rates and productivity, ease of genetic manipulation, rapid proliferation in large-scale suspension cultures and high adaptation to protein-free media. The transfection in step (1) may be carried out according to a protocol known in the art.

In the method, step (2) is directed to culturing the recombinant cell line anchoring the IDS expression vector therein in a serum-free medium. The culturing may be carried out in a medium and under conditions optimized for the kind of host cell. Preferred is a serum-free medium. Being free of sera (e.g., bovine sera), such media avoid the likelihood of inducing the side effects or risks associated with sera.

In one embodiment of the present invention, the culturing of the recombinant cell line transfected with an IDS expression vector may be further scaled up. For example, the recombinant cell line of the present invention may be cultured in a shake flask and then scaled up to hundreds to thousands of liters in a bioreactor. The culturing step is carried out in the presence of a hydrolysate, which has an important influence on the determination of formylglycine content. Preferably, the hydrolysate is added in such an amount as to form a final concentration of 0.1~10.0 g/L. The hydrolysate useful in the present invention may be those obtained by hydrolyzing an animal or plant material. More particularly, the hydrolysate may be obtained by hydrolyzing at least one selected from the group consisting of, but not limited to, soybean, potato, wheat germ, and yeast.

In the method, step (3) is directed to the purification of IDS from the cell culture through anion exchange chromatography, hydrophobic chromatography, cation exchange chromatography, and affinity chromatography.

Preferably, the four chromatographic processes may be performed in that order. However, it should be obvious to an ordinary artisan that the order may be changed if necessary. Together with the order of the chromatographic processes, the resins and the pH values of the eluting buffers are important in determining the glycosylation pattern and formylglycine content of IDS.

Anion exchange chromatography is intended to remove media components and various impurities from the cell culture and is performed on a column filled with Q SEPHAROSE® resins using an eluting buffer with a pH of from 5.5 to 7.5. In an exemplary embodiment, the eluting buffer may have a pH of 7.0±0.3.

Hydrophobic chromatography is intended to remove the media components and impurities that remain after anion exchange chromatography. It is performed on a column filled with phenyl SEPHAROSE® resins, using an eluting buffer at a pH of from 5.0 to 7.0. In an exemplary embodiment, the eluting buffer may have a pH of 5.5±0.2.

Cation exchange chromatography is intended to select high the formylglycine content and remove remaining impurities. It is performed on a column filled with cation exchange resins, using an eluting buffer with a pH of from 4.0 to 6.0. In an exemplary embodiment, the eluting buffer may have a pH of 5.3±0.2. Examples of the cation exchange resins useful in the present invention may include CM SEPHAROSE™ Fast Flow, SP SEPHAROSE™ Fast Flow, S SEPHAROSE™ Fast Flow and CAPTO™ MMC, all from GE Healthcare, but are not limited thereto. Preferably, the eluting buffer ranges in pH from 4.0 to 6.0. In an exemplary embodiment, the pH of the eluting buffer may be 5.3±0.2.

Affinity chromatography is intended to remove the residual glycerol and concentrate the volume of the eluates. It is performed on a column filled with Blue SEPHAROSE™ resins, using an eluting buffer with a pH of from 6.0 to 8.0. In an exemplary embodiment, the eluting buffer may have a pH of 6.2±0.2.

The conditions of each type of chromatography may be optimally modified by the ordinary artisan. With regard to more specific chromatography conditions, reference may be made to Example 1-5 described below.

The method for preparing the composition comprising IDS as an active ingredient in accordance with the present invention may further comprise inactivating viruses that may be incorporated into the composition. The inactivation may be conducted in various ways, and preferably by holding the culture at an acid condition, for example pH 3.0~4.0. In an exemplary embodiment, the acidic condition may be of pH: 3.7±0.05. According to another exemplary embodiment, the inactivation may be conducted by holding the culture under a high pH condition for a predetermined time. The inactivating process may be achieved during the purification process, preferably during the chromatography, and more preferably between the hydrophobic chromatography and the cation exchange chromatography.

After the chromatographic processes, the active fraction thus obtained may be concentrated and filtered to afford IDS which can be used as the active ingredient of the pharmaceutical composition.

The composition may be mixed with a pharmaceutically acceptable carrier and formulated into a suitable dosage form.

The composition comprising the IDS, prepared by the method according to the present invention, has advantages over conventional IDS compositions as follows 1) it exerts higher pharmaceutical efficacy thanks to a higher formylglycine content, 2) it can more effectively catabolize GAG accumulated within lysosomes, 3) it is free of animal-derived serum and thus safe, and 4) it is safe and efficacious thanks to its purity of 99.9% or higher.

Advantageous Effects

The composition comprising the recombinant IDS and the formulation comprising the same in accordance with the present invention are superior in pharmaceutical efficacy and safety to the conventional agent ELAPRASE® and thus can be effectively used for the therapy of Hunter syndrome.

DESCRIPTION OF DRAWINGS

FIG. 6 is a view showing the amino acid sequence of SEQ ID NO: 1 as analyzed by MALDI-MS/MS and LC-ESI-MS/MS.

FIG. 10 is a view indicating the positions of disulfide bonds in the IDS of SEQ ID NO: 1, obtained through MALDI-MS/MS.

FIG. 25B shows that GC1111 and ELAPRASE® showed a similar pattern of GAG reduction in the liver in a 24 week efficacy test in an IDS knock-out mouse.

FIG. 25C shows that GC1111 and ELAPRASE® showed a similar pattern of GAG reduction in the kidney in a 24 week efficacy test in an IDS knock-out mouse.

FIG. 25D shows that GC1111 and ELAPRASE® showed a similar pattern of GAG reduction in the heart in a 24 week efficacy test in an IDS knock-out mouse.

FIG. 25E shows that GC1111 and ELAPRASE® showed a similar pattern of GAG reduction in the spleen in a 24 week efficacy test in an IDS knock-out mouse.

MODE FOR INVENTION

Figure 1:
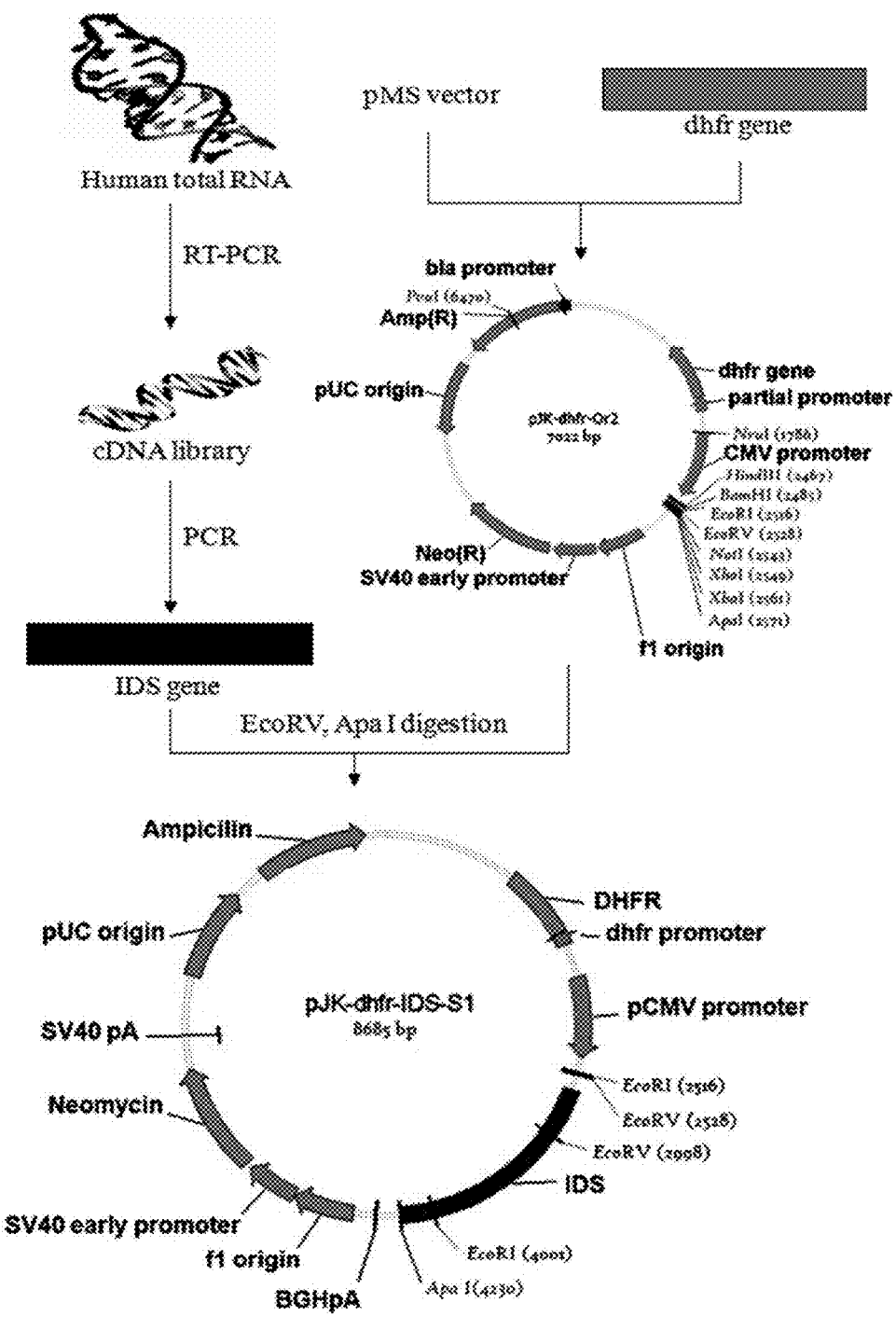
FIG. 1 is a view illustrating a scheme for constructing the pJK-dhfr-IDS-S1 vector used to construct an IDS expression vector.

A better understanding of the present invention may be obtained through the following examples which are set forth to illustrate, but are not to be construed as limiting the present invention.

According to the method below, human iduronate-2-sulfatase (IDS) was prepared by DNA recombination method. The method of preparation is briefly described in FIG. 3. The IDS prepared in accordance with the present invention was named "GC1111." Features of GC1111 and ELAPRASE®, which is currently available on the market, are compared and summarized in Table 1 below.

TABLE 1

| Category | GC1111 | ELAPRASE ® |
| --- | --- | --- |
| Manufacturer | Green Cross Corp. (GCC) | Shire |
| Generic name | Idursulfase beta | Idursulfase |
| Amino acid | 525 AAs, identical to human IDS, glycoprotein | 525 AAs, identical to human IDS, glycoprotein |
| Formulation/Dose | Liquid, 6 mg/3 mL/vial | Liquid, 6 mg/3 mL/vial |
| Host cell | CHO-DG44 | Human cell line HT-1080 |
| Expression vector | pJK-dhfr-Or2-IDS | pXI2S 1 |
| MCB/WCB preparation | Serum-free | Bovine serum used |
| Culture method | Suspension culture, fed-batch, serum-free | Continuous culture, bovine serum used |
| Distillation process | 2 UF processes, 4 column processes | 2 UF processes, 6 column processes |
| Virus inactivation process | Yes | No |
| M6P content (cellular uptake) | 3.0 mol/mol | 2.0 mol/mol |
| Formylglycine content (substrate degradation) | 80 ± 15% | 50% |
| Purity | 99.9% or higher Column, SDS-PAGE (silver, SYPRO) characterization, spatial conformation | 99.9% or higher Column, SDS-PAGE |

❑Purity >99.9%: The degree of purity of GC1111 is expected to be higher than that of ELAPRASE ® and, thus, it is predictable that the stability related with adverse effects due to the presence of impurities and the overall effectiveness thereof will be enhanced.

Based on the criteria and the testing methods of purity analysis, characterization and the study of crystallization for spatial conformation, the absolute purity of the GC1111 is expected to be at least 99.9%.

Example 1: Preparation of IDS

<1-1> Gene Acquisition

Peripheral blood mononuclear cells (PBMC) were isolated from human blood as described previously [S. Beckebaum et al., *Immunology*, 2003, 109:487-495]. Total RNA was extracted from the PBMC according to a protocol described previously [M. J. Holland et al., *Clin. Exp. Immunol.*, 1996, 105:429-435]. In order to construct a cDNA library from the total RNA, single-stranded cDNA was synthesized using oligo-(dT) primer with the aid of a single-strand synthesis kit (Boehringer mannheim). In this regard, DEPC-treated distilled water was added to an eppendorf tube containing 1 μg of the total RNA so as to form a final volume of 12.5 μL. Then, 1 μL of a 20 pmol oligo(dT) primer was added to the tube, followed by incubation at 70° C. for 2 min and cooling. To this reaction mixture were added 4 μL of a reaction buffer, 1 μL of dNTP, 1 μL of an RNase inhibitor, and 1 μL of reverse transcriptase which were then reacted at 42° C. for one hour to synthesize single stranded cDNA. PCR was performed on the cDNA as a template in the presence of primers of SEQ ID NOS: 2 to 4 to amplify a human IDS gene. In this context, each primer was designed to contain a restriction enzyme recognition site for use in gene cloning.

<1-2> Construction of Expression Vector

A. Construction of pJK-dhfr-IDS-S1 Vector

A light chain signal sequence of an antibody (derived from a part of the human IgG light chain) as a non-coding sequence was introduced into the 5'-terminus of the IDS gene acquired by Example <1-1> before PCR. After the PCR product obtained thereby was run on gel by electrophoresis, the human IDS gene was isolated using a gel extraction kit. The isolated IDS gene and the pJK-dhfr-Or2 vector (Aprogen) were digested with EcoRV and ApaI and ligated to each other at 16° C. for 20 hours. The recombinant vector thus constructed was transformed into *E. coli* (DH5α) which was then spread over an LB plate containing 50 μg/mL ampicillin and incubated overnight. Colonies grown on the plates were selected and cultured so as to isolate the plasmid therefrom (FIG. 1).

B. Construction of Recombinant Human IDS Expression Plasmid

In order to change the non-coding sequence of the plasmid constructed above to a signal sequence, the recombinant human IDS was subcloned to a pJK-dhfr-or2 vector. To this end, the pJK-dhfr-IDS-S1 vector was digested with EcoRV and ApaI to give a partial IDS gene (1233 bp) which was then inserted into the pJK-dhfr-Or2 vector previously treated with the same restriction enzymes, to construct a pJK-dhfr-IDS-S2 vector. In order to introduce a non-coding sequence and a signal sequence to the 5'-terminus, an IDS N1 forward primer (SEQ ID NO: 5) and an IDS 4 reverse primer (SEQ ID NO: 7) were used for PCR with the pJK-dhfr-IDS-S1 vector serving as a template. After starting at 94° C. for 5 min, PCR was performed with 30 cycles of 94° C. for 1 min, 55° C. for 30 sec and 72° C. for 40 sec and finished by extension at 72° C. for 10 min.

The PCR amplification afforded a partial IDS gene that was 448 bp. This gene was used as a template for the PCR which was performed again in the presence of an IDS N2 forward primer (SEQ ID NO: 6) and an IDS 4 reverse primer (SEQ ID NO: 7) under the same conditions as described above. This resulted in the synthesis of a DNA fragment 476 bp long.

Figure 2:
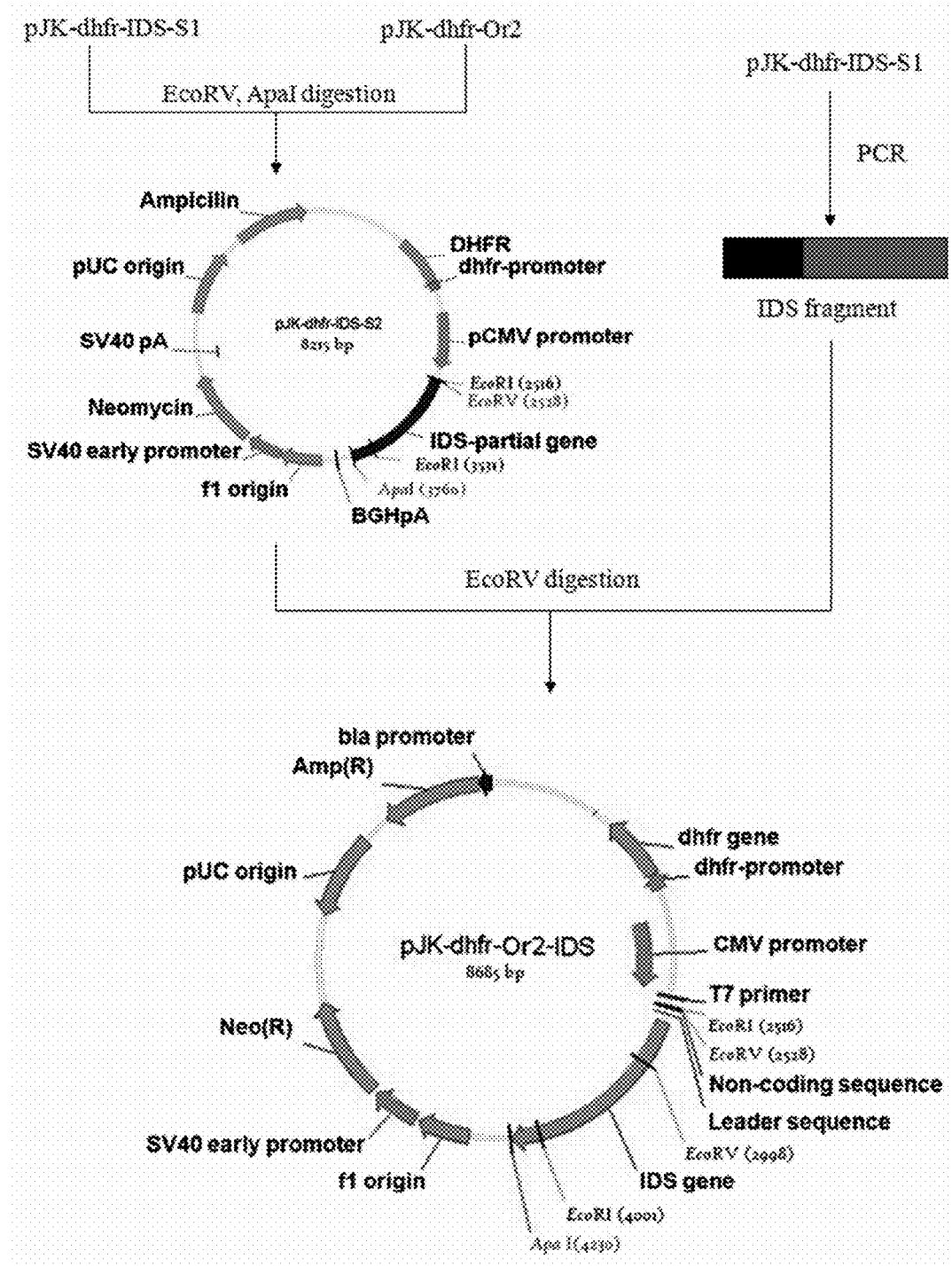
FIG. 2 is a view illustrating a scheme for constructing the IDS expression vector pJK-dhfr-Or2-IDS from the pJK-dhfr-IDS-S1 of FIG. 1.

Subsequently, the pJK-dhfr-IDS-S2 vector and the recombinant human IDS gene fragment (476 bp) were separately digested with EcoRV. The digests were separated on gel by electrophoresis to obtain the vector and the 476 bp-long IDS fragment. These vector and insert were ligated at 16° C. for 12 hours in the presence of T4 DNA ligase to construct pJK-dhfr-Or2-IDS plasmid. These procedures are illustrated in FIG. 2.

To confirm the construction of the IDS expression plasmid, DH5α was transformed with pJK-dhfr-Or2-IDS and cultured for 24 hours on an LB plate containing ampicillin (50 μg/mL). From the colonies thus formed, a plasmid was isolated and digested to measure the size of the insert. Also, base sequencing was conducted using a T7 primer (SEQ ID NO: 8).

<1-3> Selection of Recombinant Human IDS Expression Cell Line

A. Transfection of CHO-DG44

CHO-DG44 was used as a host cell for expressing the IDS of the present invention. The mutant Chinese hamster ovary cell CHO-DG44 carries a double deletion for the endogenous dhfr (dihydrofolate reductase) gene which encodes DHFR enzyme. The DHFR enzyme is involved in the conversion of folate through dihydrofolate (FH2) into tetrahydrofolate (FH4) which is involved in the de novo synthesis of nucleic acids. The level of dhfr in the cells is dependent on the concentration of MTX. MTX, which is structurally similar to folic acid, a substrate of DHFR, competes with folic acid for binding dihydrofolate reductase, so that most dihydrofolate reductase loses its activity in the presence of MTX. Hence, if cells do not amplify a sufficient amount of dhfr, they die because they cannot synthesize nucleic acids necessary for their life. In contrast, if the amplification is sufficient, the cells can survive under a high concentration of MTX because they are relatively abundant in dhfr. This system may be applied to animal cells to select a transfected cell line which can amplify the dhfr gene and thus a structural gene of interest.

To this end, a dhfr gene was introduced as an amplifiable marker into the IDS expression vector pJK-dhfr-Or2-IDS, constructed in Example 1-2, and gene amplification was conducted using MTX and the dhfr gene.

In this regard, the DG44 cell line (obtained from Dr. Chaisin, Columbia University) was suspended in 10 mL of DMEM/F12 (supplemented with nucleotides and nucleosides, and 10% fetal bovine serum (FBS)) and harvested by spinning at 1000 rpm for 5 min. The cells were inoculated into 50 mL of a culture medium in a T-175 flask and incubated at 37±1° C. in a 5±1% $CO_2$ incubator. One day before transfection, the culture medium for DG44 cells was removed from the T-175 flask and the cells were washed twice with PBS and detached by trypsinization. Then, they were seeded at a density of $5×10^5$ cells into a T-25 flask and cultured at 37±1° C. for 24 hours in a 5±1% $CO_2$ incubator. Bacterial or fungal contamination was examined under an optical microscope while PCR-ELISA was performed to examine whether the cells were contaminated with mycoplasma.

The germ-free DG-44 cells were transfected with the IDS expression vector pJK-dhfr-Or2-IDS, constructed in Example 1-2, using a Lipofectamine kit. In this regard, 5 μg of the expression vector and 50 μL of Lipofectamine were separately diluted in 800 μL of Opti-MEM I, mixed carefully so as not to form bubbles, and left at room temperature for 15 min. Meanwhile, DG44 cells were washed once with sterile PBS and three times with Opti-MEM I. To the DG44 cells were carefully added the DNA-lipofectamine mixture and then 6.4 mL of Opti-MEM before incubation at 37±1° C. for 5 hours in a 5±1% $CO_2$ incubator. Thereafter, the incubation was conducted for an additional 48 hours in the medium supplemented with 8 mL of DMEM/F12 and 1.6 mL of FBS to promote the recovery of cell membranes and the growth of cells.

B. Selection of Geneticin (G418)-Resistant Cell Line

The cultured cells were detached with 0.25% trypsin, counted, and seeded at a density of $5×10^3$ cells/well into 96-well plates containing 100 μL of MEM-alpha medium (supplemented with 10% dialyzed FBS and 550 μg/mL G418) per well. Next day, the same medium was added in an amount of 100 μL/well and the cells were cultured for 2-3 weeks to form colonies. When the cells grew to 50% confluency, the medium was replaced with a fresh one. After maintenance for 3 days, the culture media were collected for enzyme analysis.

The medium was replaced with 200 μL of a fresh medium every three days. On day 3~4 after culturing, non-transfected cells, that is, cells that were not resistant to geneticin started to detach from the bottom of the 96-well plates when observed with an optical microscope. The selected clones were cultured while being sequentially transferred from the 96-well plates to 24-well plates, 6-well plates and 100-mm dishes in the order. When the cells grew to 80~90% confluency in 100-mm dishes, the expression level was measured again. The cells were detached with 0.25% trypsin, counted and plated at a density of 5×10⁵ cells/well/3 mL into 6-well plates, maintained for 3 days and counted. The expression level of the protein was quantitatively analyzed. According to the analysis results, 15 clones were selected.

C. Selection of IDS Expression Cell Line with High Productivity

The 15 selected clones were cultured at an increased concentration of MTX to select cell lines in which IDS was amplified.

In this context, the cells were inoculated at a density of 1×10⁶ cells/100 mm dish/10 mL of a medium containing MTX and cultured to 80~90% confluency. One tenth of the volume of the cell culture was inoculated again into 100 mm dish/10 mL. This sub-culturing process was repeated twice. The cells were allowed to undergo at least three passages so that they were sufficiently adapted to increased MTX concentrations. The concentration of MTX was increased, from 5 nM for the clones selected after conducting an analysis for the first three days, to 20 nM. In each step, the clones adapted to the increased MTX concentration were cultured for three days to measure cell growth rates. IDS expression levels were measured to select cell lines in which the amplification of the IDS gene took place, that is, cell lines in which the recombinant IDS was expressed at a high rate. Of the selected cell lines, NI4 was used in subsequent experiments because it had the highest expression level.

D. Selection of Single Cell by Limiting Dilution

There was the possibility that the cell line NI4 might have become mixed with other cell lines. Hence, the cell line was separated into a single cell line. The N14 clones which survived 20 nM MTX were subcloned through limiting dilution so as to select a desired cell line.

First, NI4 was inoculated at a density of 0.5 cells/well into IMDM medium (Gibco BRL, Cat#12200) in 96-well plates and cultured with the medium replenished every three days. On day three, the plates were observed under a microscope to exclude the wells in which two or more colonies had been formed per well. The wells in which only one colony had formed per well were selected and continued to be cultured. After culturing for 15 days, the cells were sub-cultured to 96-well plates and when cells had grown to 90% confluency, the medium was freshly replenished.

A total of 263 single cell lines were identified from the N14 cell line. Of them, cell line S46 was found to have the highest IDS activity and named NI4-S46.

<1-4> Cell Culture

A. Shake Flask Culture

The NI4-S46 cell line was cultured on a large scale to produce the IDS of the present invention. The cell line was inoculated into an EX-cell 302 serum-free medium (containing glutamine, dextran sulfate, and poloxamer 188 in 125 mL culture flasks and cultured at 37±1° C. in a 5±1% $CO_2$ incubator. Subsequently, the cells were passaged at a ratio of 1:1~1:8 every two to three days using shake flasks. Upon the passage, the culture volume was gradually increased to approximately 2,400 mL. In many shake flasks, the cells were cultured to a level sufficient to be inoculated into a bioreactor.

B. Culture in 30 L Bioreactor (Working Volume 20 L)

When the density of the cells in the shake flasks reached 1.3×10⁶ cells/mL, they were inoculated into a 30 L bioreactor. During cell culturing, the culture conditions were kept at a dissolved oxygen content of 10% or higher, a culture temperature of 37±1° C. and a pH of 7.0±0.2. If necessary, cell samples were taken and observed under a microscope. The cell culture was examined to analyze cell count, cell viability, pH, glucose concentration and glutamine concentration. On the basis of the analysis results, when it was decided that the cells were sufficiently grown, the cells were inoculated into a 150 L bioreactor.

C. Culture in 150 L Bioreactor (Working Volume 100 L)

When the cells in a 30 L bioreactor reached a density of 0.9×10⁶ cells/mL or higher, they were inoculated into a 150 L bioreactor. During cell culturing, the culture condition was kept at a dissolved oxygen content of 10% or higher, a culture temperature of 37±1° C. and a pH of 7.0±0.2. If necessary, cell samples were taken and observed under a microscope. The cell culture was examined to analyze cell count, cell viability, pH, glucose concentration and glutamine concentration. On the basis of the analysis results, when it was decided that the cells were sufficiently grown, the cells were inoculated into a 650 L bioreactor.

D. Culture in 650 L Bioreactor (Working Volume 500 L)

When the cells in a 150 L bioreactor reached a density of 0.9×10⁶ cells/mL or higher, they were inoculated into a 650 L bioreactor. During cell culturing, the culture condition was kept at a dissolved oxygen content of 10% or higher, a culture temperature of 34±1° C. and a pH of 6.9±0.2 for three days and then, at a culture temperature of 32±1° C. and a pH of 6.9±0.2. If necessary, cell samples were taken and observed under a microscope to analyze cell counts, cell viability, pH, glucose concentrations and glutamine concentrations. Depending on the analysis result, glucose and glutamine concentrations were adjusted to continue cell growth. During the culturing, a hydrolysate was added to increase the formylglycine conversion.

<1-5> Purification of IDS

IDS was isolated from the cell culture using a series of the following four chromatographic processes.

A. Harvest and Filtration of Culture Medium

When the cell viability remained in the range of 80~85% 10 days after inoculation into the 650 L bioreactor, culturing was stopped. The cells were harvested from the culture using the Millipore POD filter system and DOHC filter (Millipore) at a pressure of 0.9 bar or less. After the cells were removed, the supernatant was filtered through a pre-filter (Millipore, 0.5±0.2 μm) and a 0.45±0.2 μm filter and recovered in a disposable sterile bag. The harvested culture solution was stored at 2~8° C.

B. Concentration and Diafiltration

The filtrate recovered in A was about 10-fold concentrated using an ultrafiltration system (Tangential Flow Filtration Membrane System). The membrane (cutoff: 30K, Pall) installed inside the ultrafiltration system was washed with WFI (water for injection) at a flow rate of 20~25 L/min and then equilibrated with a buffer (pH 7.0±0.3) containing 20 mM sodium phosphate (sodium dihydrogen phosphate monohydrate and sodium hydrogen phosphate heptahydrate). After equilibration, the filtrate was fed into the membrane while recovering the fractions that did not pass the membrane. Once the recovered volume became about ¹⁄₁₀ of the initial volume of the filtrate, the concentration procedure was stopped. The buffer was consecutively exchanged in a volume three to four times as large as that of the concentrate. If the conductivity and the pH fell within the criteria, the process was stopped. [criteria—conductivity: ≤5.0 mS/cm, pH 7.0±0.2.

C. Anion Exchange Chromatography

To remove media component and various impurities from the concentrate recovered in B, anion exchange chromatography was conducted on a column (GE Healthcare) filled with Q Sepharose resins (GE Healthcare). The column was equilibrated with equilibrium buffer (pH 7.0±0.3) containing 20 mM sodium phosphate (sodium dihydrogen phosphate monohydrate and sodium hydrogen phosphate heptahydrate). The concentrate obtained in B was filtered through a 0.45±0.2 μm filter (Sartorius) and loaded at a flow velocity of 100~120 cm/h into the equilibrated column. After the loading was completed, the column was primarily washed with the equilibrium buffer and then with washing buffer (pH 7.0±0.3) containing sodium chloride. Subsequently, a target protein was eluted with an eluting buffer (pH 7.0±0.3) containing sodium chloride.

D. Hydrophobic Chromatography

To remove the media component and impurities that remained after anion exchange chromatography, hydrophobic chromatography was performed on a column (GE Healthcare) filled with phenyl Sepharose resins (GE Healthcare). The column was equilibrated with equilibrium buffer (pH 6.0±0.3) containing sodium chloride. The eluate obtained in C was filtered through a 0.45±0.2 µm filter (Sartorius) and loaded at a flow velocity of 70~100 cm/h into the equilibrated column. After the loading was completed, the column was washed with the equilibrium buffer. Subsequently, a target protein was eluted with an eluting buffer (pH 5.5±0.2) containing glycerol.

E. Inactivation of Virus by Low pH

Viruses that may be derived from host cells or any material used in the processes carried out were inactivated by a low pH condition. In this regard, the eluate obtained in D was maintained for 2 hours at an acid condition (pH: 3.7±0.05) of which acidity was adjusted with 25% acetic acid. Thereafter, the pH of the eluate was increased to pH: 4.3±0.2 using 0.5 M sodium hydroxide for use in the next process. The inactivation by low pH was conducted at 12±2° C.

F. Cation Exchange Chromatography

IDS is glycoprotein with oligosaccharides, and exists as an isomer that has a different isoelectric point according to the content of sialic acid at the end of the Glycan chain. As oligosaccharides with a negative charge, sialic acid shows a difference in terms of the degree of binding to cation exchange resin according to the content of sialic acid. Using this characterization, cation exchange chromatography was conducted to obtain IDS showing high activity (a high content of formylglycine) with a high content of sialic acid and to remove other impurities [Product impurity (Aggregated IDS, processed IDS), process impurity (Host Cell protein)]. In detail, a column filled with cation exchange Capto™ MMC resins (GE Healthcare) was equilibrated with glycerol-added equilibration buffer (pH 4.3±0.2). The inactivated eluate obtained in E was filtered through a 0.45±0.2 µm filter (Sartorius) and loaded at a flow velocity of 100~120 cm/h onto the equilibrated column. Subsequently, the column was washed with the equilibration buffer, followed by elution with glycerol-added eluting buffer (pH 5.3±0.2) to give IDS with a high sialic acid content (isoelectric point 3.5 or less), high activity (formylglycine content: 80±15%) and high purity (SE-HPLC, 98% or higher).

G. Affinity Chromatography

Affinity chromatography (Blue SEPHAROSE®, GE Healthcare) was conducted to remove the glycerol used in the cation exchange chromatography and to reduce the volume of the eluate. The eluate obtained in F was filtered through a 0.45±0.2 µm filter (Sartorius) and loaded at a flow velocity of 100~120 cm/h onto a Blue SEPHAROSE® resin-filled column (GE Healthcare) that was previously equilibrated with glycerol-added equilibration buffer (pH 4.5±0.2). After completion of the loading, the column was washed with washing buffer (pH 4.5±0.2) and the target protein was eluted with eluting buffer (pH 6.2±0.2).

H. Concentration and Buffer Exchange

An ultrafiltration system (Tangential Flow Filtration Membrane System) was used to adjust the protein concentration of the eluate obtained in G and to exchange the buffer of the purified protein with formulation buffer. The membrane (cutoff: 10K, Pall) installed inside the ultrafiltration system was washed with WFI (water for injection) at a flow rate of 450~650 mL/min and then equilibrated with a formulation buffer (2.25 g/L sodium dihydrogen phosphate monohydrate, 0.99 g/L sodium hydrogen phosphate heptahydrate, 8 g/L sodium chloride, pH 6.0±0.2) without polysorbate 20, followed by concentrating the target protein. The buffer was consecutively exchanged in a volume three to four times as large as that of the concentrate. If the conductivity and the pH fell within the criteria, the process was stopped. [criteria—conductivity: 15.0±3.0 mS/cm, pH 6.0±0.2]. Adjust the content of the concentrated solution to 4.0±0.5 mg/mL.

I. Nanofiltration

Using a nano filter (NFP, Millipore), nano filtration was performed to remove viruses that might have come from the host cells or any of the materials used. Integrity test for filter is performed after washing the nano filter with water for injection. Once the integrity test was passed, the nanofilter was equilibrated with 1 L of formulation buffer (2.25 g/L sodium dihydrogen phosphate monohydrate, 0.99 g/L sodium hydrogen phosphate, 8 g/L sodium chloride, pH 6.0±0.2) without polysorbate 20. After completion of equilibration, the concentrate obtained in H was passed through the filter at a pressure of about 2 bar to produce a nanofiltrate. After filtration was completed, the filter was washed with the formulation buffer (post wash solution). After combining the nano filtration solution and the post wash solution, protein content is measured.

J. Drug Substance

The protein concentration of the filtrate obtained in I was adjusted with formulation buffer without polysorbate 20. After the addition of polysorbate, the solution was filtered through a 0.2 µm filter to produce a drug substance. The drug substance was aliquoted and stored in a deep freezer (−70±10° C.) until use.

K. Drug Product (Filling, Labeling, Packaging)

The stock stored in a deep freezer was thawed in a water bath maintained at 28±1° C. and diluted to a protein concentration of about 2.05±0.2 mg/mL using formulation buffer (2.25 g/L sodium dihydrogen phosphate monohydrate, 0.99 g/L sodium hydrogen phosphate heptahydrate, 8 g/L sodium chloride, 0.23 g/L polysorbate 20, pH 6.0±0.3) Thereafter, the dilution solution was filtered through a 0.2 µm filter to produce a final bulk solution. This final bulk solution was filled in 6 mL vial with approximately 3.3 g using auto filling. Once an vial inspection test was passed, the vials were packed to produce a drug product.

Figure 3:
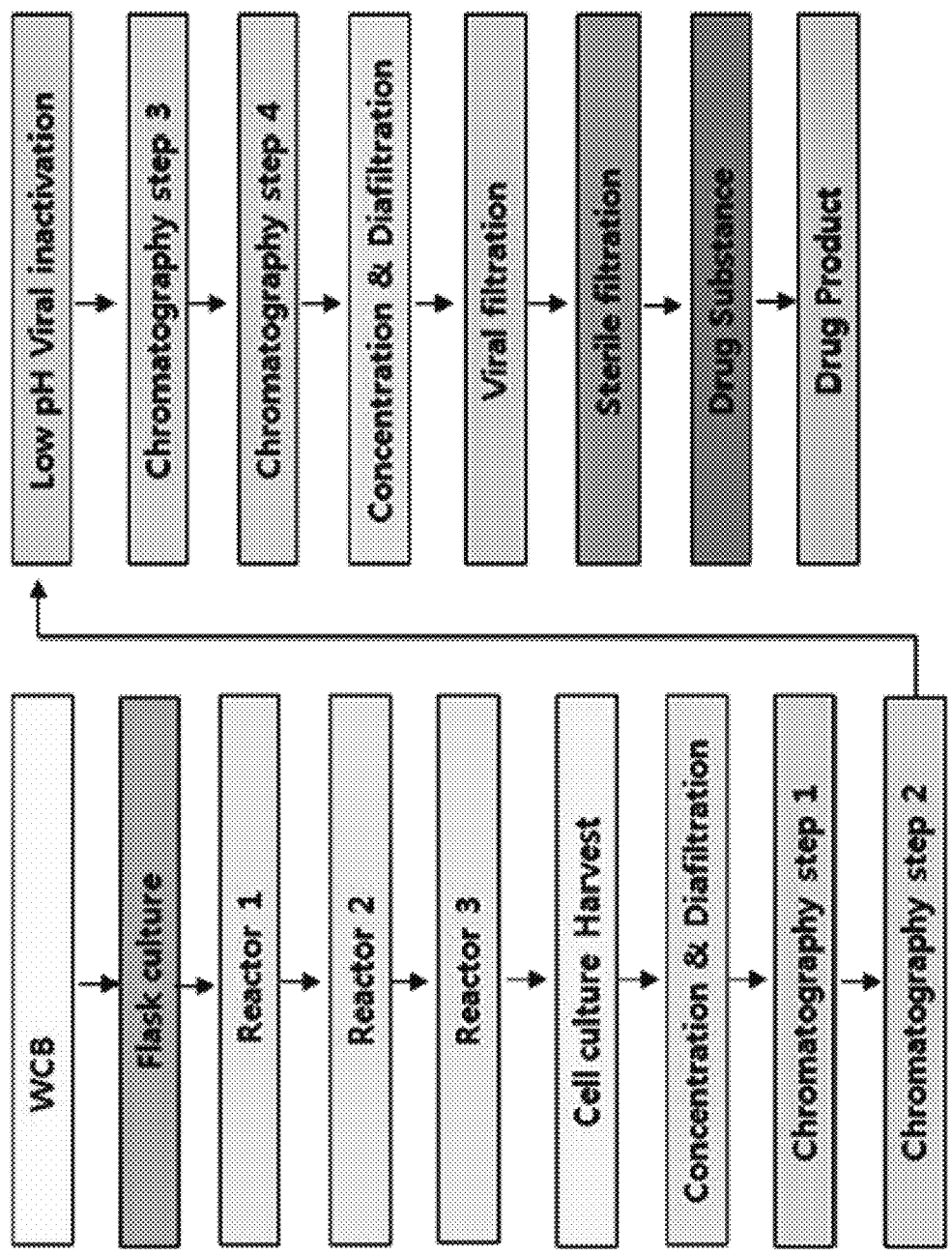
FIG. 3 is a flow chart illustrating the isolation and purification of IDS from transfected CHO-DG44.
Figure 4:
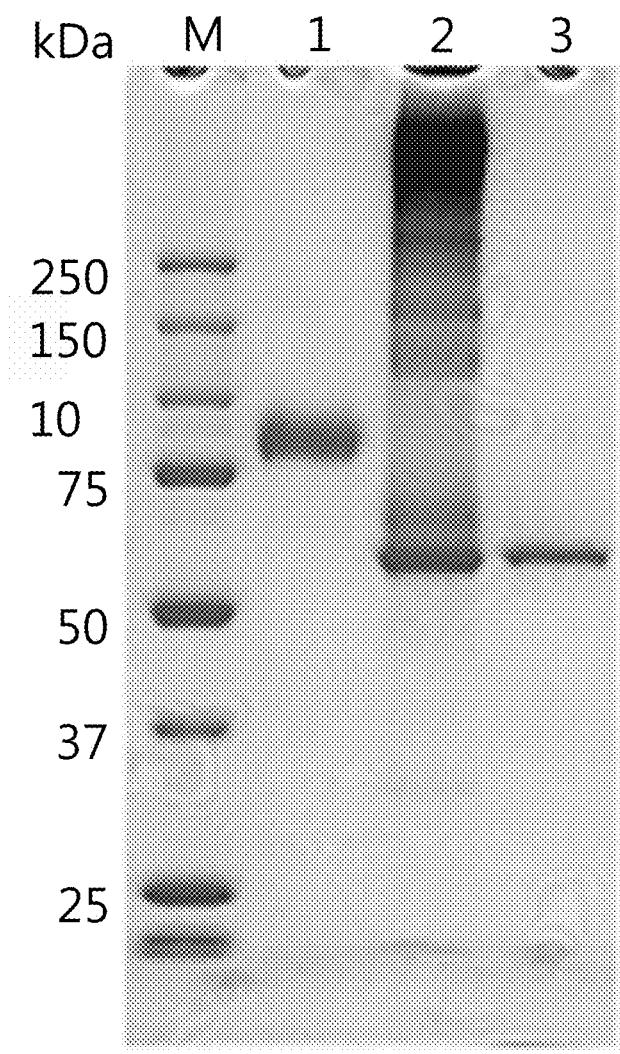
FIG. 4 is a photograph showing an SDS-PAGE result of IDS for analyzing the N-terminal sequence where a marker was run on lane M, glycosylated IDS on lane 1, PNGase F on lane 2, and deglycosylated IDS on lane 3.

The procedure from cell line culturing to final product production is illustrated in FIG. 3.

Comparative Example 1: Preparation of ELAPRASE®

ELAPRASE®, commercially available recombinant IDS, was used as a comparative example.

Figure 5:
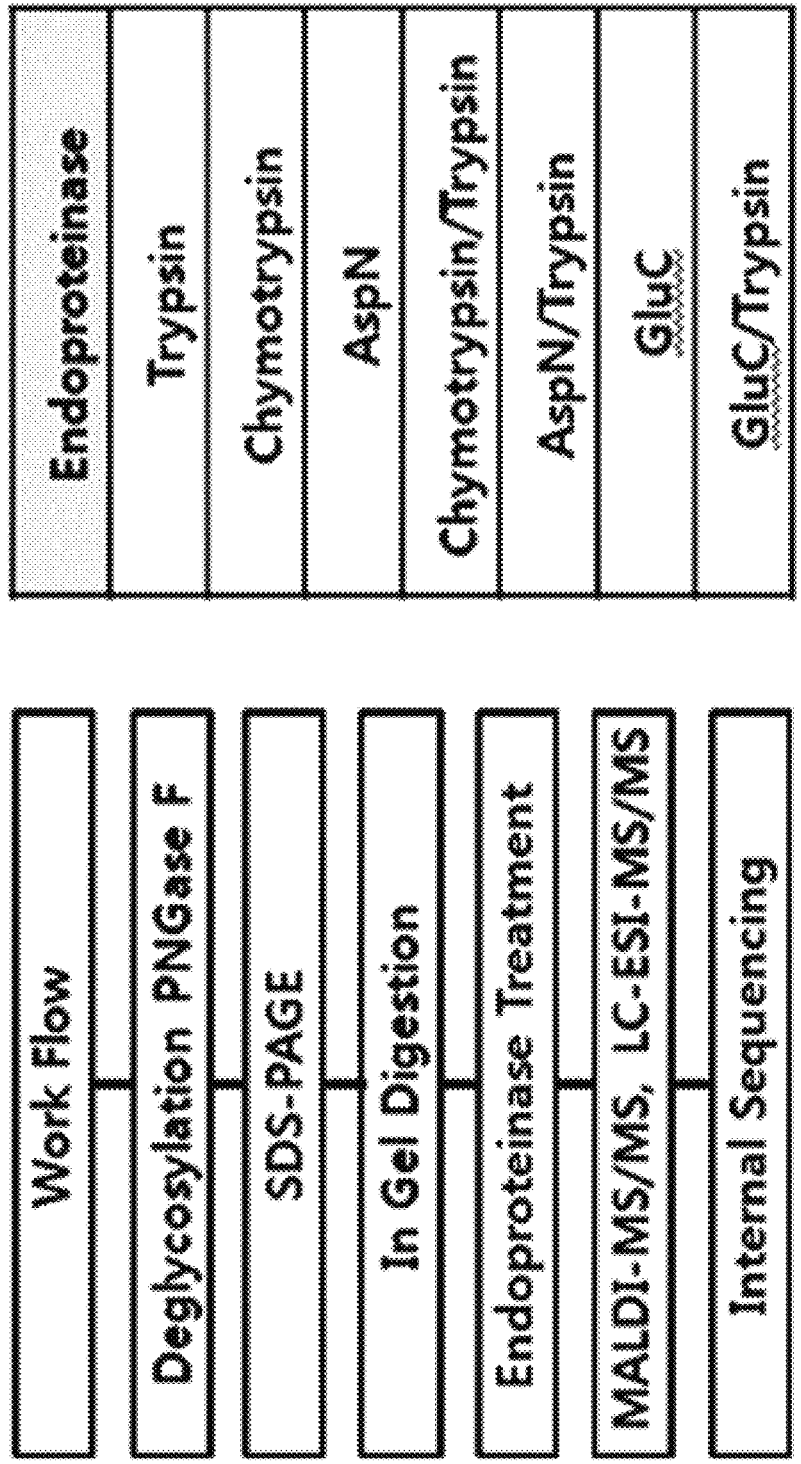
FIG. 5 is a flow chart illustrating the process of analyzing the amino acid sequence of IDS.

Experimental Example 1: Structural Analysis and Characterization of Inventive IDS <1-1> Amino Acid Sequencing—Internal Sequencing Deglycosylated IDS was separated by SDS-PAGE, followed by gel slicing. Then, digests resulting from treatment with various endoproteinases (trypsin, chymotrypsin, AspN, chymotrypsin/trypsin, AspN/trypsin, GluC and GluC/trypsin) were analyzed using MALDI-MS/MS and LC-ESI-MS/MS (FIG. 5). As a result, a total of 525 amino acid sequences were identified. The amino acid sequences coincided with the theoretical sequence of human IDS (FIG. 6).

<1-2> Disulfide Bond Analysis

Figure 7:
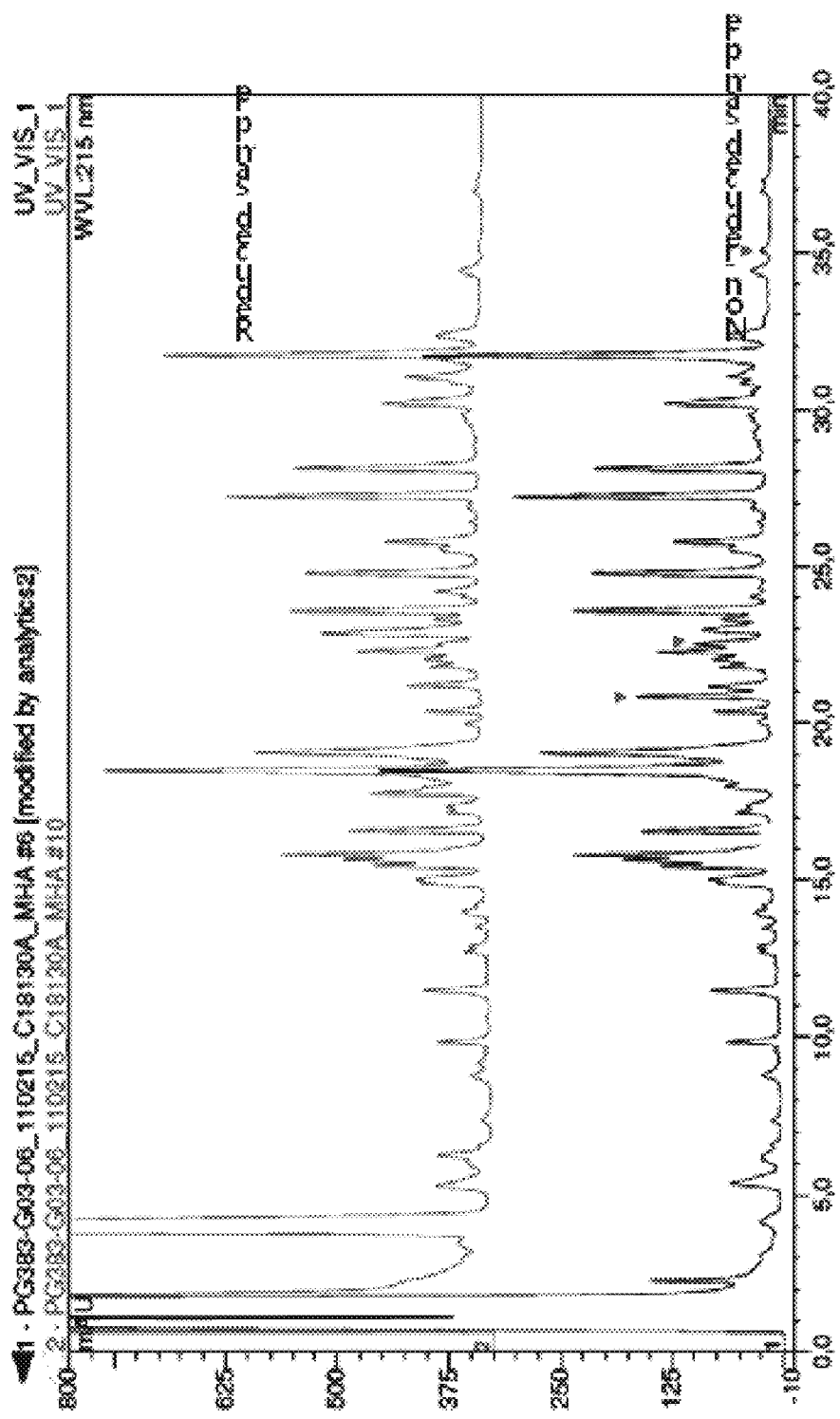
FIG. 7 is an RP-HPLC chromatogram of non-reduced and reduced IDS samples showing the position of disulfide bonds in IDS.

In a polypeptide, a disulfide bond is a covalent linkage, usually derived by the coupling of two SH groups of cysteine residues, playing an important role in stabilizing the higher structure of proteins. Theoretically, the 525 amino acids of IDS contain six cysteine residues, four of which form disulfide bonds. In this example, the location of cysteine residues responsible for the disulfide bonds of IDS was identified. First, IDS was deglycosylated by treatment with PNGase F to exclude the interference of sugars. In order to prevent the cysteine residues that do not take part in the formation of disulfide bonds from acting as an interfering factor, 4-vinylpyridine was used to convert IDS into a non-reduced sample so that the SH groups are restrained from randomly forming S—S bonds. Meanwhile, the disulfide bonds were cleaved by DTT, followed by blocking with 4-vinylpyridine to give a reduced sample. Trypsin and AspN, selected on the result of Experimental Example 1-3, were applied to the non-reduced and the reduced sample. The peptide fragments thus obtained were separated by RP-HPLC. RP-HPLC chromatograms of the non-reduced and the reduced samples were compared so as to discriminate the peaks that were found in the non-reduced sample, but not in the reduced sample (FIG. 7).

Figure 8:
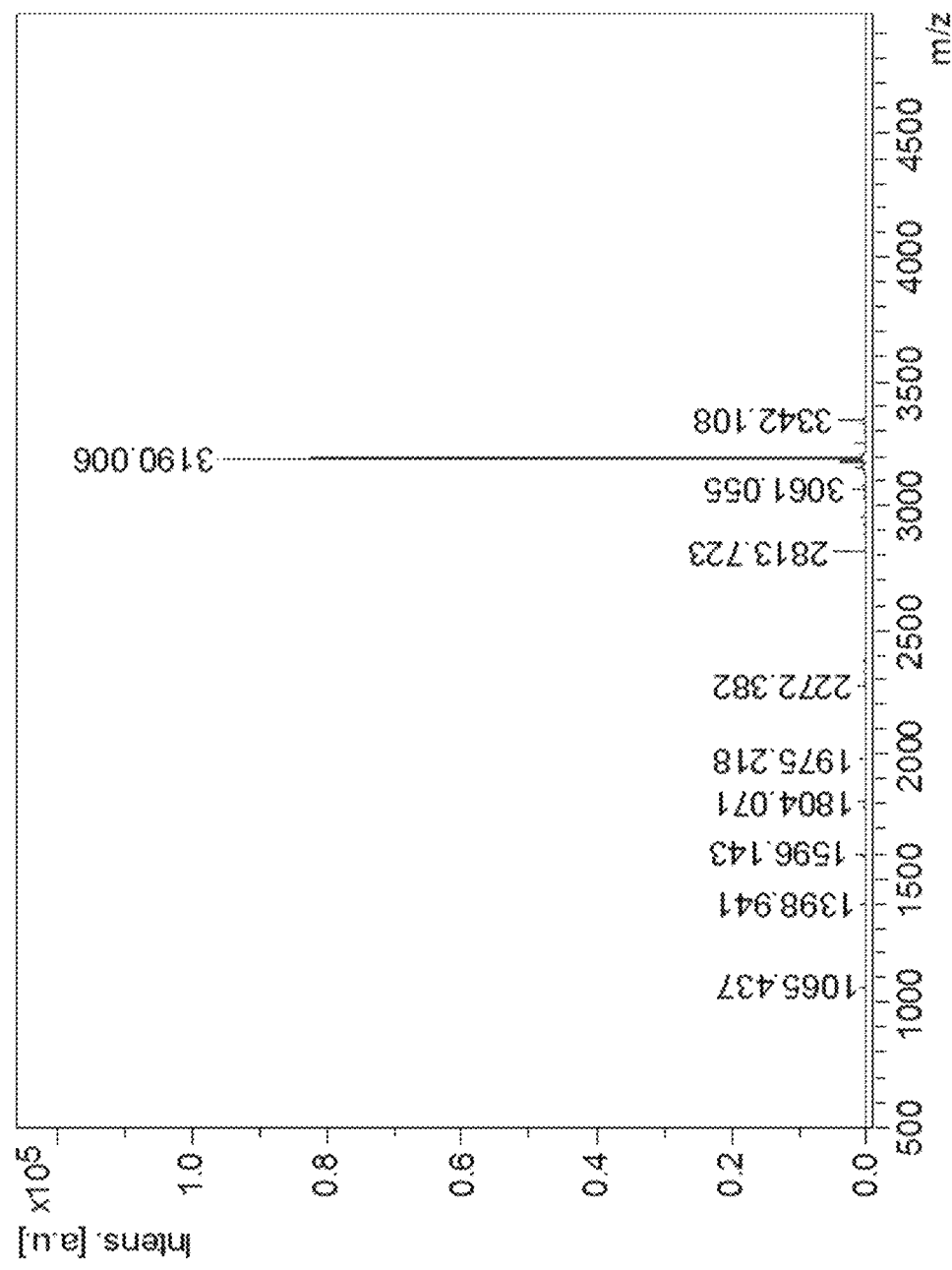
FIG. 8 is a view showing the positions of disulfide bonds in the IDS of the present invention as analyzed by MALDI-MS.

For more exact analysis, fractions at the discriminated peaks were reduced in size by additional treatment with endoproteinases, and the peaks containing disulfide bonds were analyzed using MALDI-MS (FIG. 8).

Figure 9:
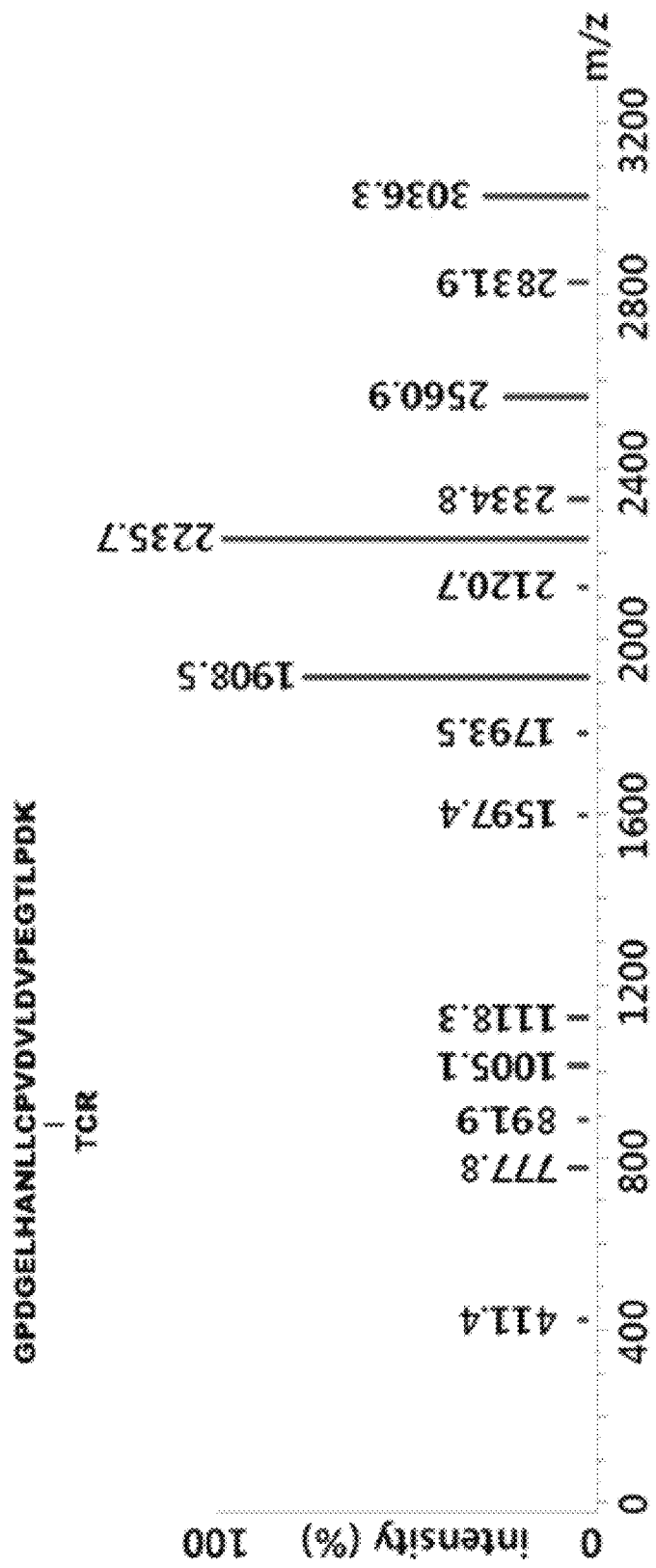
FIG. 9 is a view showing the positions of disulfide bonds in the IDS of the present invention as analyzed by MALDI-MS/MS.

Peaks with disulfide bonds were again sequence analyzed using MALDI-MS/MS (FIG. 9) to examine the positions of cysteine residues that form disulfide bonds among the 525 IDS amino acid residues. As shown in FIG. 10, disulfide bonds were observed to form between C146-C159 and between C397-C407.

<1-3> Analysis of Formylglycine Content

IDS degrades heparan sulfate and dermatan sulfate, both of which are a kind of glycosaminoglycan (GAG). This degradation activity is not acquired until the cysteine residue at position 59 in the active site (Cys59) is converted into formylglycine (FGly) by post-translational modification. Thus, the degradation activity of IDS was analyzed by examining the post-translational modification of Cys59 to FGly. For this analysis, AQUA (absolute quantification), a quantitative analysis method based on MS (Mass Spectroscopy), was used, in which a radio-labeled synthetic substrate (AQUA peptide) was spiked into a sample. To quantitatively analyze formylglycine at Cys59 position, a serial dilution of AQUA peptide was spiked into a sample and a calibration curve was drawn. Ratios of FGly-type peptide to Cys-type peptide were measured by LC-ESI-MS analysis, and applied to the AQUA calibration curve to calculate the content of formylglycine.

This analysis determined the conversion of Cys59 to FGly at a rate of 80±15%. In consideration of the Cys59 to FGly conversion rate of about 50% in the commercially available agent ELAPRASE® (Elaprase Science Discussion, EMEA, 2007; Genet Med 2006:8(8):465-473), the therapeutic composition comprising the IDS of the present invention and the formulation prepared with the composition is anticipated to have much higher therapeutic activity compared to ELAPRASE®.

<1-4> Identification of Glycosylation Pattern

An assay was performed to examine whether the IDS of the present invention is glycosylated and to identify the glycosylation pattern if any. To this end, IDS was treated with various glycoside hydrolase enzymes, the digests were separated on by SDS-PAGE and their motility patterns were analyzed.

In detail, IDS samples were digested with combinations of the following four glycoside hydrolase enzymes and separated by SDS-PAGE.

TABLE 2

Properties of Sugar Cleaving Enzymes

| | Function/Property |
|---|---|
| PNGase F | Cleaves a sugar moiety (N-glycan) from protein Asn at the cleavage site is converted into Asp |
| Endo H | Cleaves a sugar moiety (N-glycan) from protein unlike PNGase F, Endo H acts on oligosaccharides of high-mannose type and hybrid type |
| O-Glycosidase | Cleaves a sugar moiety (O-glycan) from protein |
| Sialidase | Cleaves terminal sialic acid residues of N-glycan or O-glycan |

Figure 11:
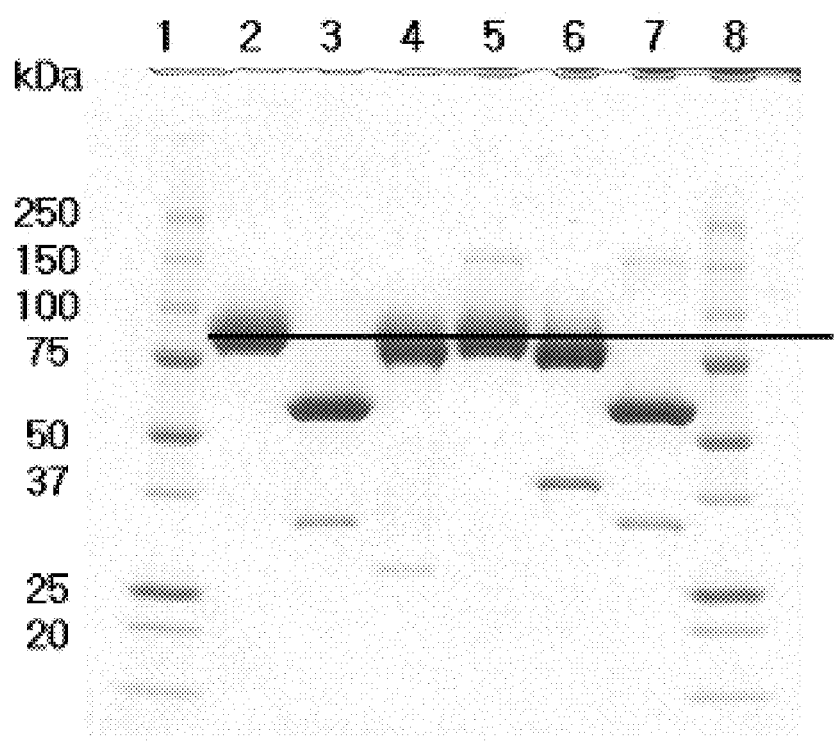
FIG. 11 is a photograph showing IDS run by SDS-PAGE after treatment with various glycoside hydrolase enzymes to examine the glycosylation of the IDS of the present invention.

As can be seen in FIG. 11, the IDS of the present invention was cleaved by PNGase F and Endo H, but not by O-glycosidase, indicating that the IDS of the present invention is an N-glycosylated protein. In addition, the IDS was completely cleaved by PNGase F, but its size reduction was slight upon treatment with Endo H. PNGase F acts on the glycosylation sites of all the three patterns whereas Endo H acts on the glycosylation sites of high-mannose type and hybrid type. Taken together, these results indicate that the IDS contains the three glycosylation patterns complex, high-mannose and hybrid.

<1-5> Analysis of Mannose-6-Phosphate Content

Binding to a M6P receptor on cells, mannose-6-phosphate (M6P) allows IDS to be internalized into cells and thus to hydrolyze heparan sulfate or dermatan sulfate in lysosomes. In this Example, IDS was acid hydrolyzed with trifluoroacetic acid (TFA) and subjected to HPAEC-PAD (Bio-LC) to quantitatively analyze mannose-6-phosphate.

Figure 12:
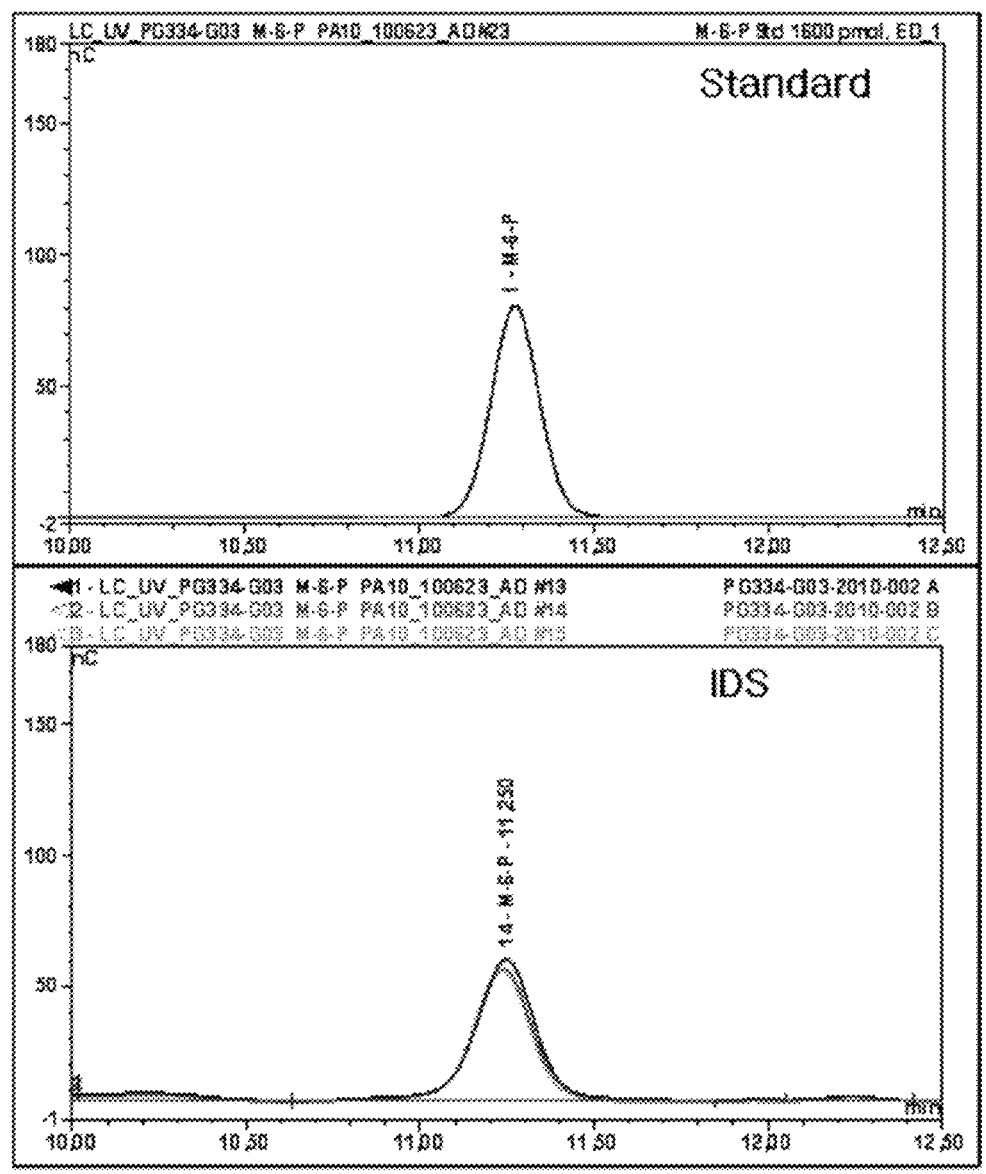
FIG. 12 is of HPAEC-PAD chromatograms showing the content of mannose-6-phosphate in the IDS of the present invention.

IDS was hydrolyzed with 6.75M TFA and the hydrolysate was analyzed using liquid chromatography (High Performance Anion-Exchange Chromatography with Pulsed Amperometric Detection; HPAEC-PAD). M6P concentration of which was already known was analyzed under the same condition, and molar ratios of M6P to glycoprotein were obtained by comparison of the areas. Analysis was conducted in triplicate. M6P standard materials and M6P composition chromatograms of the IDS are shown in FIG. 12 and the molar ratios of M6P are summarized in Table 3, below.

TABLE 3

Analysis Results for Mannose-6-phosphate Content

| Run No. | M-6-P Ret. time (min) | Amount pmol/25 µl M-6-P | Amount pmol/25 µl Protein | Ratio M-6-P/ Protein (mol/mol) |
|---|---|---|---|---|
| 13 | 11.25 | 1320.59 | 428 | 3.09 |
| 14 | 11.23 | 1241.31 | 428 | 2.90 |
| 15 | 11.23 | 1245.83 | 428 | 2.91 |
| Average | 11.24 | 1269.25 | 428 | 2.97 |
| CV | 0.09% | 3.51% | | 0.11 |

As is understood from the data of Table 3, there are approximately 3 moles of M6P per mole of IDS. From these results, it is inferred that the therapeutic composition comprising the IDS of the present invention and the formulation prepared with the composition have a high ability to catabolize GAG accumulated in lysosomes.

<1-6> Mass Analysis

Masses of glycosylated IDS and deglycosylated IDS were measured using MALDI-TOF-MS. Treatment of glycosylated IDS with PNGase F afforded deglycosylated IDS. MALDI-TOF-MS was performed using Voyager-DE PRO Biospectrometry (Applied Biosystems, USA) coupled with a delayed Extraction laser-desorption mass spectrometer. The instrument was normalized with bovine serum albumin and IgG1. Analysis results are summarized in Table 4, below.

TABLE 4

MALDI-TOF-MSMALDI-TOF-MS Analysis Results of IDS

Glycosylated IDS

| m/z | Charge (z) | Protein Mass (Da) | Remark |
|---|---|---|---|
| 25646 | 3 | 76935 | |
| 38708 | 2 | 77414 | |
| 77360 | 1 | 77359 | |
| 154533 | 1 | 77266 | dimer |
| Average | | 77244 ± 210 | |

Deglycosylated IDS

| m/z | charge (z) | Protein Mass (Da) | remark |
|---|---|---|---|
| 29767 | 2 | 59532 | |
| 34655 | | | PNGase F |
| 59313 | 1 | 59312 | |
| 118706 | 1 | 59353 | dimer |
| Average | | 59399 ± 120 | |

| Sample | Molecular Weight |
|---|---|
| Theoretical | 59298 Da |
| Glycosylated | 77244 ± 210 Da |
| Deglycosylated | 59399 ± 120 Da |

As apparent from the data of Table 4, the molecular size is 77,244 Da for glycosylated IDS and 59,399 Da for deglycosylated IDS, which is similar to the molecular weight calculated on the basis of the amino acid sequence, which is 59,298 Da.

<1-7> Purity Measurement

The purity of IDS was measured using size exclusion chromatography. Size exclusion chromatography is a chromatographic method in which molecules in solution are separated by their relative molecular weight and shape. In size exclusion chromatography, proteins larger than the pore size of the column cannot penetrate the pore system and pass through the column at once. Subsequently, the analytes with smaller molecular weights or sizes elute later. For this chromatography, Alliance 2695 HPLC system (Waters, Wis., USA) coupled with 2487 UV/VIS detector (Waters, Wis., USA) was employed. Proteins were detected at 214 nm, and analyzed using Empower 2 Software. The analytes were loaded onto a TSK G3000SWXL column linked to a TSK SWXL guard column (Tosoh, Japan). IDS, after being diluted to a concentration of 1.0 mg/mL in a formulation buffer, was loaded in a volume of 10 μL onto the column. They were allowed to flow with mobile phase (20 mM sodium phosphate buffer, 200 mM NaCl, pH 7.0) at a flow rate of 0.5 mL/min for 60 min.

Figure 13:
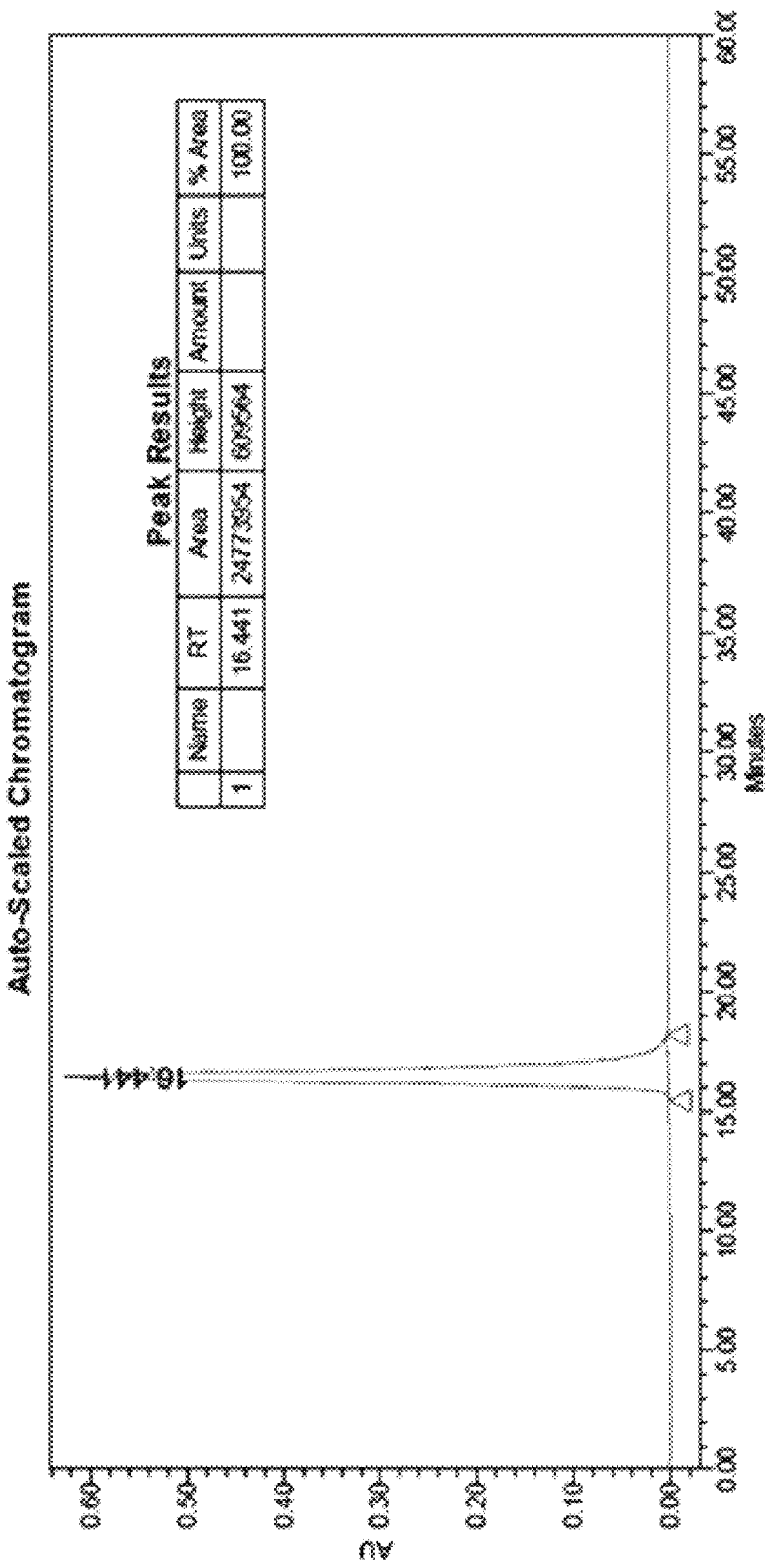
FIG. 13 is a size exclusion chromatogram showing the purity of the IDS of the present invention.

Analysis results are shown in FIG. 13. As can be seen, IDS monomers had a retention time of approximately 16.4 min, and were eluted with 100% purity.

<1-7a> Purity Measurement (2)

Reversed-phase high-performance liquid chromatography (RP-HPLC) involves the separation of molecules on the basis of hydrophobicity. The separation depends on the hydrophobic binding of the solute molecule from the mobile phase to the immobilized hydrophobic ligands attached to the stationary phase.

TABLE 5

RP-HPLC Operation Conditions

| Mobile Phase | A: Water + 0.1% (v/v) TFA |
| | B: Acetonitrile + 0.1% (v/v) TFA |
| Column | Phenomenex Jupiter C4 (4.6 × 250 mm, 5 μm) |
| Flow Rate | 0.8 mL/min |
| Temperature | Column: 30° C., Sampler: 4° C. |
| Injection Volume | 10 μL |
| Detector | 214 nm |
| Run Time | 90 min |

| Gradient | Time | Flow rate | % A | % B |
|---|---|---|---|---|
| | 0 | 0.8 | 70 | 30 |
| | 10 | 0.8 | 70 | 30 |
| | 70 | 0.8 | 30 | 70 |
| | 75 | 0.8 | 10 | 90 |
| | 80 | 0.8 | 70 | 30 |
| | 90 | 0.8 | 70 | 30 |

<1-8> Activity Measurement Using Synthetic Substrate

The reaction of IDS with the synthetic substrate (4-methylumbelliferylα-L-idopyranosiduronic acid-2-sulfate sodium salt (4MU-IdoA-2S)) for 4 hours releases the sulfate moiety (primary reaction). After the primary reaction, the addition of recombinant human α-L-iduronidase (rh IDUA) induces a secondary enzymatic reaction with the substrate 4-methylumbellifery-L-iduronide (reactant left after the release of the sulfate moiety in the primary reaction) to separate the 4-methylumbelliferyl moiety from the L-iduronide moiety. Because the remaining 4-methylumbelliferyl is fluorogenic, the activity of IDS was evaluated by measuring the intensity of fluorescence (Ex.355 nm/Em.460 nm). The IDS of the present invention was found to range in specific activity from 19 to 55 nmol/min/μg. The IDS of the present invention was found to range in specific activity from 30.0 to 70.0 nmol/min/μg. This activity indicates that formylglycine exists in the active site of the enzyme as a result of the post-translational modification of the cysteine residue at position 59 in IDS.

<1-8a> Activity Measurement Using Synthetic Substrate (2)

The reaction of IDS with the synthetic substrate (4-methylumbelliferylα-L-idopyranosiduronic acid-2-sulfate sodium salt (4MU-IdoA-2S)) for 90 minutes releases the sulfate moiety (primary reaction). After the primary reaction, the addition of recombinant human α-L-iduronidase (rh IDUA) induces a secondary enzymatic reaction with the substrate 4-methylumbellifery-L-iduronide (reactant left after the release of the sulfate moiety in the primary reaction) to separate the 4-methylumbelliferyl moiety from the L-iduronide moiety. Because the remaining 4-methylumbelliferyl is fluorogenic, the activity of IDS was evaluated by measuring the intensity of fluorescence (Ex.355 nm/Em.460 nm). The IDS was found to range in $K_m$ from 170 to 570 μM and in $k_{cat}$ from 4,800 to 16,200 $min^{-1}$. This activity indicates that formylglycine exists in the active site of the enzyme as a result of the post-translational modification of the cysteine residue at position 59 in IDS.

<1-9> Activity Measurement Using Natural Substrate

In order to determine whether the reaction with the IDS and natural substrate, the sulfate ions released from the substrate (heparin disaccharide) by reaction with IDS were measured. The reaction mixture was loaded onto an ion column (Vydac 302IC) and allowed to flow with the mobile phase of 0.49 g/L phthalic acid at a flow rate of 2 ml/min, during which free sulfate ions were detected at 290 nm in negative mode.

Figure 14:
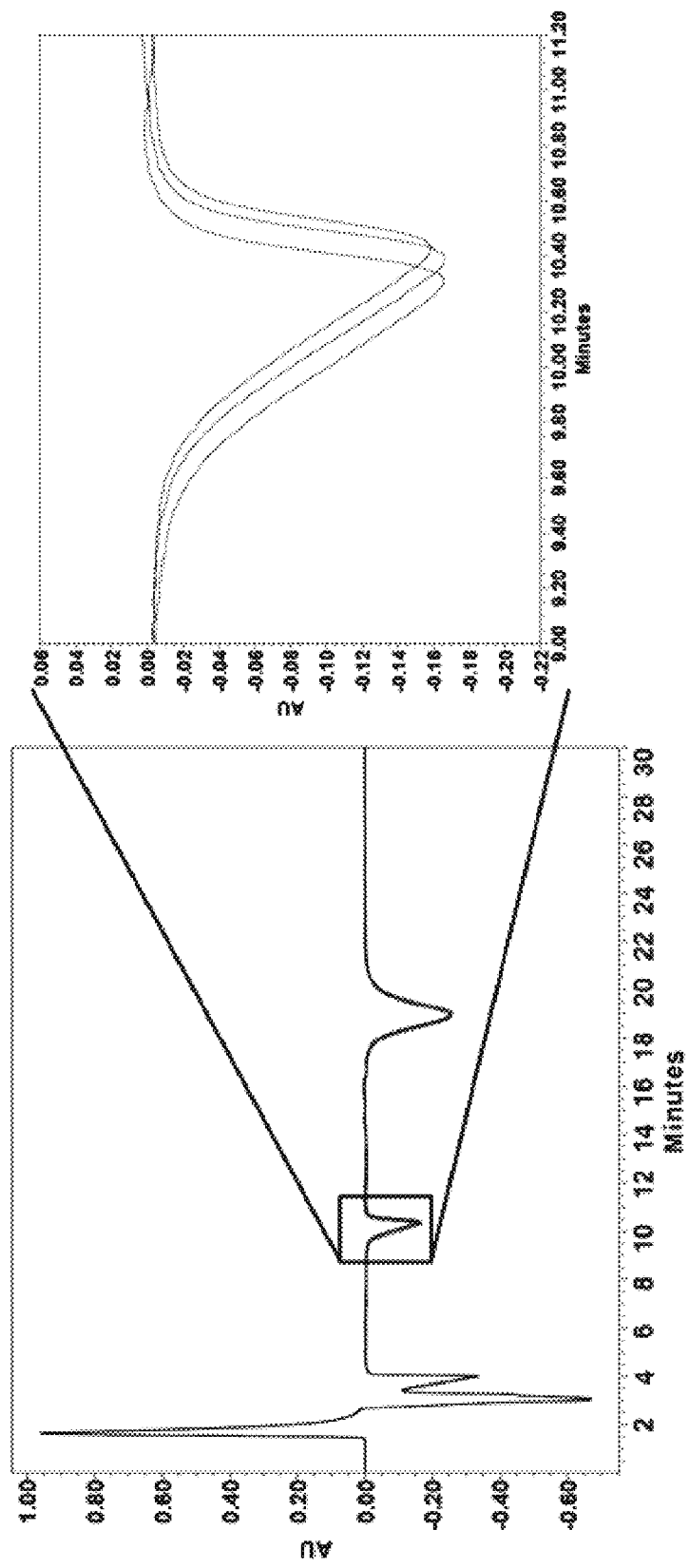
FIG. 14 is an ion chromatogram showing the catalytic activity of the IDS of the present invention on a natural substrate.

As shown in FIG. 14, the IDS was confirmed to hydrolyze sulfate ion from heparin disaccharide, indicating that the IDS is capable of degrading O-linked sulfate of dermatan sulfate and heparan sulfate in vivo.

<1-10> In Vivo Cellular Uptake Activity

Hunter syndrome (MPS II) is one type of lysosomal storage disorders (LSD); and in enzymatic replacement therapy for the treatment of LSD, IDS must be picked up by cells of a patient and enter into a lysosome to degrade glycosaminoglycans (dermatan sulfate and heparin sulfate).

Binding to M6P receptor on cells, mannose-6-phosphate (M6P) which are located on IDS allow IDS to be internalized into cells. In this Example, IDS was subjected to HPAEC-PAD (Bio-LC) to quantitatively analyze mannose-6-phosphate. As a result, it was confirmed that there is approximately 3.0 moles of M6P per mole of IDS. Also, cellular uptake activities were analyzed by assaying normal fibroblast cells and Hunter syndrome patient cells.

The cellular internalization activity of the IDS was measured using the normal fibroblast cells and Hunter syndrome patient cells. In this regard, normal fibroblast cells and Hunter syndrome patient cells (obtained from Samsung Medical Center, Seoul, Korea) were cultured and allowed to be internalized into cells while they were incubated with various concentrations of IDS at 37° C. for 20 hours in a 5% $CO_2$ incubator. After being harvested, the cells were lyzed, and the level of the IDS internalized into the cells was determined in the lysate.

Figure 15:
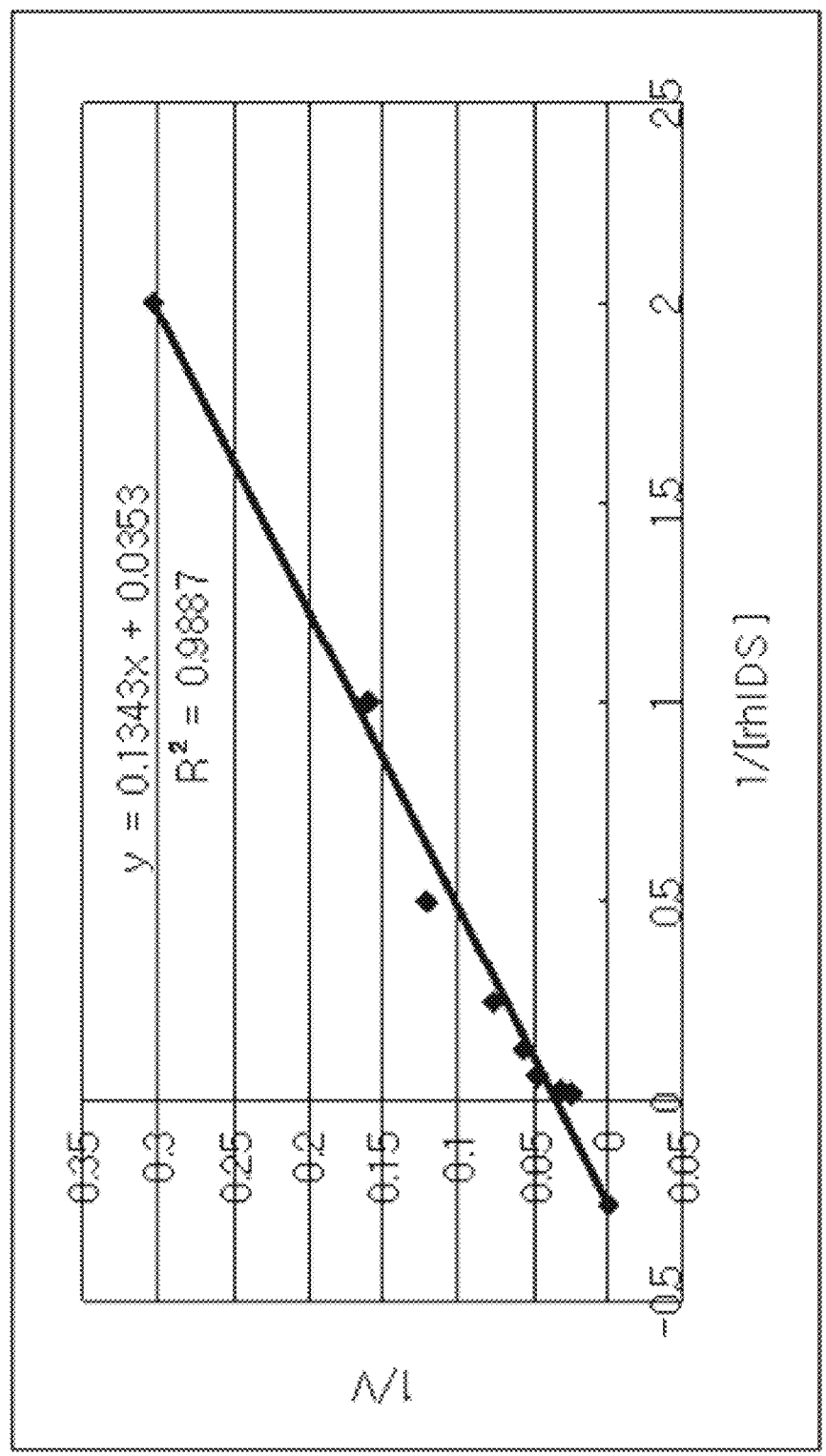
FIG. 15 is Lineweaver-Burk plot showing ratios of cellular uptake amounts of IDS relative to amount of IDS added to normal fibroblast cells.

On the basis of the concentration ratio of internalized IDS to IDS added to the normal fibroblast cells, a Michaelis-Menten graph and a Lineweaver-Burk plot were constructed from which $K_{uptake}$ (IDS concentration at which the reaction rate is half of the maximum rate achieved at saturating substrate concentrations) was calculated. $K_{uptake}$ was calculated to be 18.0 nM or less, indicating that IDS is internalized into cells by the binding of the M6P of IDS to M6P receptors on the cell surface (FIG. 15).

Figure 16:
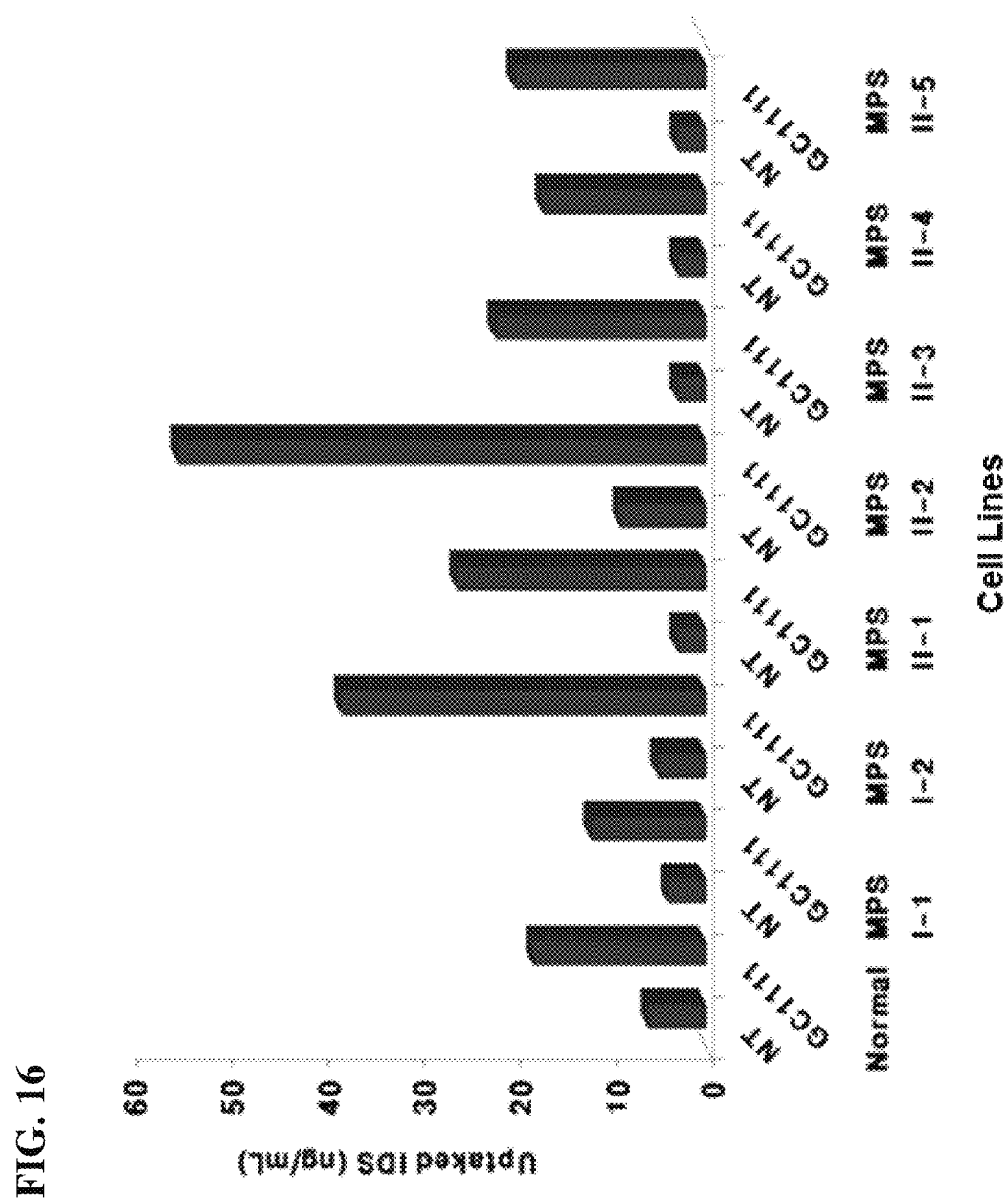
FIG. 16 is a graph showing the amount of the IDS of the present invention internalized into normal human fibroblast cells and the cells of patients suffering from Hunter syndrome.
Figure 17:
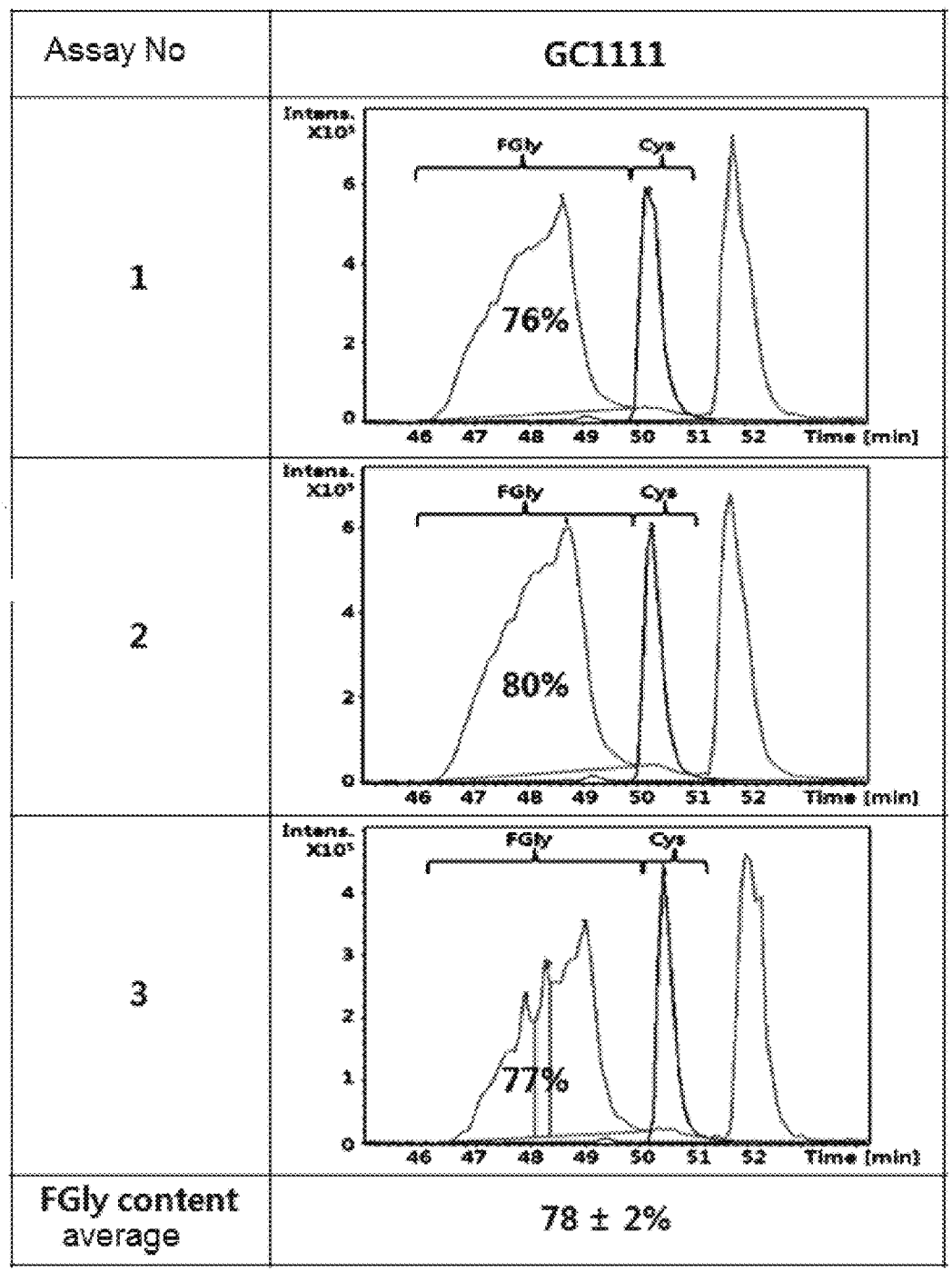
FIG. 17 is a view showing measurements of the formylglycine content in the IDS of the present invention.
Figure 18:
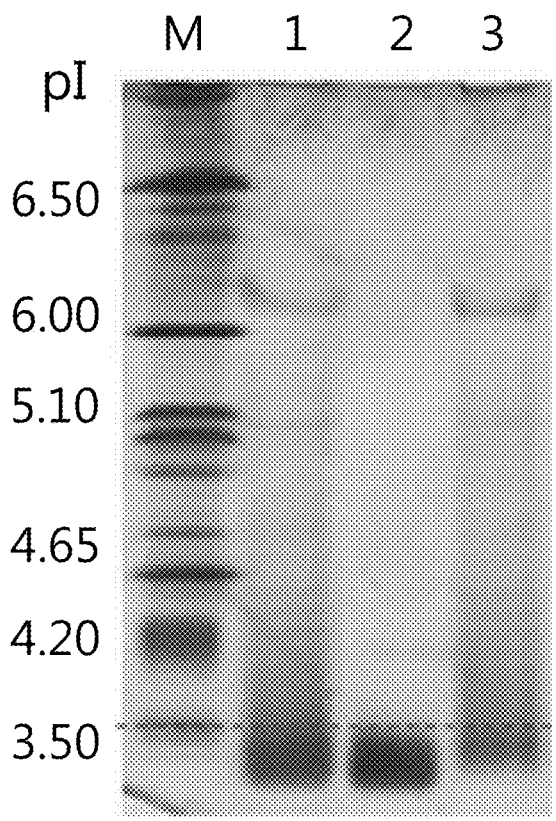
FIG. 18 is a view showing IEF (isoelectric focusing) points of the IDS of the present invention before and after cation exchange chromatography wherein M is run on M lane, a loaded sample for cation exchange chromatography on lane 1, an eluate of cation exchange chromatography on lane 2, and a regeneration solution after cation exchange chromatography on lane 3.

Also, the cellular uptake and activity of IDS in Hunter syndrome patient cells as well as normal human fibroblast cells were analyzed. The uptake and activity of the IDS were increased in both the cells, demonstrating that the IDS of the present invention is more efficiently internalized into cells (FIG. 16).

<1-10a> In Vivo Cellular Uptake Activity (2)

The cellular internalization activity of the IDS was measured using the normal fibroblast cells and Hunter syndrome patient cells. In this regard, normal fibroblast cells and Hunter syndrome patient cells (obtained from Samsung Medical Center, Seoul, Korea) were cultured and allowed to be internalized into cells while they were incubated with various concentrations of IDS at 37° C. for 6 hours in a 5% $CO_2$ incubator. After being harvested, the cells were lyzed, and the level of the IDS internalized into the cells was determined in the lysate.

On the basis of the concentration ratio of internalized IDS to IDS added to the normal fibroblast cells, a Michaelis-Menten graph and a Hanes-Woolf plot were constructed from which $K_{uptake}$ (IDS concentration at which the reaction rate is half of the maximum rate achieved at saturating substrate concentrations) was calculated. $K_{uptake}$ was calculated between 3.0 nM and 23.0 nM, indicating that IDS is internalized into cells by the binding of the M6P of IDS to M6P receptors on the cell surface (FIG. 15).

Also, the cellular uptake and activity of IDS in Hunter syndrome patient cells as well as normal human fibroblast cells were analyzed. The uptake and activity of the IDS were increased in both the cells, demonstrating that the IDS of the present invention is more efficiently internalized into cells (FIG. 16).

<1-11> Determination of Host Cell-Derived DNA Contents

According to the recommendation from the World Health Organization (WHO), Guidelines on the Quality, Safety, and Efficacy of Biotherapeutic Protein Products Prepared by Recombinant DNA Technology, adopted by the $64^{th}$ meeting of the WHO Expert Committee on Biological Standardization, 21-25 Oct. 2013, the level of cell-derived and plasmid-derived DNA should be not more than 10 ng per purified dose.

The contents of host cell-derived DNA contents were measured on the IDS composition obtained in Example 1 <1-5>, using a Threshold system (Threshold total DNA assay kit, Molecular Devices Corp). Threshold system is equipment for the determination of total DNA quantity. It is intended for use in screening for total DNA contamination of recombinant DNA. In the first step, DNA was isolated from the proteins in the sample. In the second step, the sample is heat denatured to convert all DNA to the single stranded form. The denatured DNA samples are incubated with the DNA labeling reagent, which contains a conjugated enzyme. In the third step, the labeled DNA is captured onto a membrane by filtration. In the last step, enzyme-catalyzed pH response is measured on captured membranes.

A standard curve was obtained using standard solutions of concentrations of 6.25, 12.5, 25, 50, 100, 200, and 400 pg/ml.

Aliquots of the purified IDS composition obtained in Example <1-5-J> and the zero calibrator were dispensed to a pair of 2 mL sterile Sarstedt microcentrifuge tube with cap, and 50 uL of spike solution (1 ng/mL) was added to one of the tube. 20 uL of Sodium N-Lauroyl Sarcosinate solution to the tube and mix, following by adding 500 uL of NaI solution containing glycogen to the mixture, vortex and then incubate at about 40° C. for about 15 minutes. 900 uL of isopropanol is added to the mixture, vortex and then let stand at room temperature for about 15 minutes, followed by centrifugation to obtain a pellet containing DNA and glycogen.

The pellet is reconstituted using a calibrator buffer (500 uL), and subject the resulting sample to denaturation and labeling. The labeled DNA was captured onto a membrane by and the enzyme-catalyzed pH response was measured on the captured membranes. The host-cell derived DNA was measured in a range of 0-0.03 ng/mg, which is far lower than the limit 1.6 ng/mg set by the FDA.

<1-12> Determination of Host Cell-Derived Protein Contents

The level of host-cell proteins should be not more than parts per million, for biological medicines used chronically over a lifetime (e.g. human insulin, erythropoietin or factor VIII). E.g., TGA Guidance 18. Australian Government, Version 1.0, August 2013).

The contents of host cell-derived protein were measured on the purified IDS composition obtained in Example 1 <1-5>, using two-site immunoenzyme assay (ELISA). Aliquots of the composition obtained in Example 1 were reacted with an affinity purified capture antibody (anti-CHO HCP antibody, Rabbit 3). An IDS-specific HCP assay kit (Young In Frontier, Korea) was used for this purpose, which allows a test performed in microtiter wells coated with an anti-CHO HCP capture antibody. The complex was reacted with anti-CHO HCP antibody (Rabbit 7)-biotin labeled antibody and then reacted with Avidine linked Horse Radish Peroxidase. The sandwich complex was reacted with TMB substrate after the microtiter strips were washed to remove and unbound reactants.

A dilution buffer (10 mg/ml BSA in TBS) was used to dilute the samples. The following reagents were used:
(a) 1× wash buffer
Mix 10× wash buffer 100 ml with distilled water 900 ml and make it to 1× washing solution
Store at 4° C. for 1 month.
(b) Working secondary antibody solution (Dilution fold may be changed, if necessary)
Add secondary antibody/AV-HRP dilution buffer 150 pi to a vial containing freeze-dried secondary antibody and mix well to obtain 100× diluted secondary antibody solution.
Add secondary antibody solution (100×) 40 uL to secondary antibody/AV-HRP dilution buffer 3,960 uL and mix well.
(c) Working AV-HRP solution
Add AV-HRP concentrated solution (100×) 40 uL to Secondary antibody/AV-HRP dilution buffer 3,960 uL and mix well.

As standard solutions, solutions containing standard CHO HCP in an amount of 0, 0.78, 1.56, 3.125, 6.25, 12.5, 25, and 50 ng/mL were prepared.

The results show that the host cell derived proteins in the samples were in a range of 0-13.7 ng/mg (=1-13.7 ppm), which is far lower than the limit of 100 ppm set by the FDA.

<1-13> Determination of Sialic Acid Contents

Sialic acid is a generic term for derivatives of neuraminic acid having a nine-carbon backbone, which is a monosaccharide with a complex structure including carboxylate, ketone and acetamide. The presence of carboxylates in sialic acid is of great importance because they are widely distributed in non-reducing terminus of glycoprotein and give acidic characteristics.

The contents of sialic acid of the IDS in the composition obtained in Example 1 <1-5>, were measured. Aliquots of the test composition were diluted with distilled water to a final concentration of 1.0 mg/ml. Standard solutions were prepared by dissolving N-acetylneruaminic acid in distilled water to make 10 mg/ml, and diluting it with distilled water to final concentrations of 0, 20, 40, 60, 80, 100, 1000, and 10,000 ug/ml.

Figure 22:
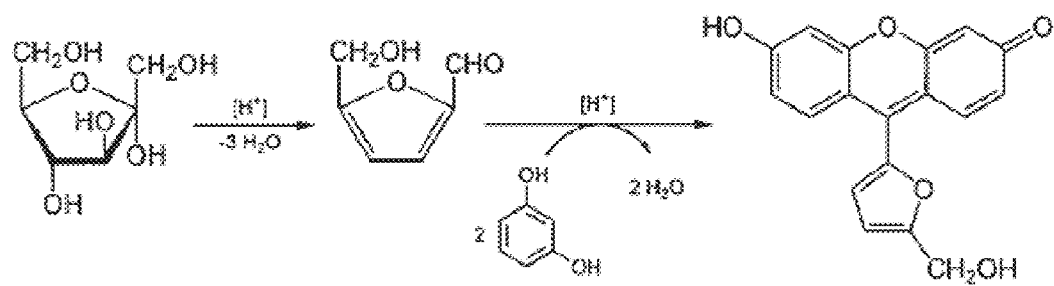
FIG. 22 shows the resorcinol method (Seliwanoff's test) used to quantify the amount of sialic acid in IDS (sialic acid causes color formation in the resorcinol method).

In the first analysis, the amount of sialic acid in IDS was quantified based on the fact that sialic acid causes color formation in the resorcinol method (Seliwanoff's test, FIG. 22). The assay was conducted in Green Cross Corp. A standard sialic acid concentration of which was already known was analyzed by measuring absorbance at 580 nm after reacting with resorcinol to obtain a standard curve. Then, IDS was allowed to react with resorcinol, and sialic acid concentration thereof was analyzed by measuring absorbance at 580 nm. As shown in Table 6, there are approximately 16.5 moles of sialic acid per mole of IDS.

Seliwanoff reaction: 100 ul of standard solutions and test solutions, respectively, were loaded to glass cab tubes, and 1 ml of resorcinol reagent (prepare by mixing hydrochloride acid R1 80 ml, 0.1M cupric sulfate 0.25 ml and 2% resorcinol solution 10 ml, and filling up to 100 ml with distilled water) was added and mixed. The resulting mixtures were incubated at 100-105° C. heating block for about 30 min. and cooled for about 10 min immediately after heat processing.

Extraction: 2 ml of extraction solution (butanol 24 ml and butyl acetate 96 ml) was added to each tube. When layers were completely separated by oxidizing at room temperature for about 30 min, transfer 1.5 ml of the supernatant to 1.5 ml tube and centrifuged for 3 min (12,000 rpm, room temperature). Adjust zero point with 'standard H' and the absorbance at 580 nm was measured.

A standard curve for the absorbance values of standard solutions and sialic acid's concentration (ug/ml) in the test solutions from the standard curve.

309 g/mol: Molecular weight of sialic acid
78,000 g/mol: Molecular weight of IDS $$\text{Sialic acid(mol)} = \frac{\text{sialic acid contents of sample solution}(\mu g/mL) \times 78000 \text{ g/mol}}{\text{sample protein concentration}(1000 \ \mu g/mL) \times 309 \text{ g/mol}}$$

The results showed that the sialic acid contents in the samples were in a range of 13.5-17.8 mol/mol, falling within the acceptance criteria of 11-20 mol/mol.

TABLE 6

Analysis results for sialic acid (Resorcinol method)

| | Batch No. | | | | | Average (mol/ mol) |
|---|---|---|---|---|---|---|
| | 20R | 707R9001 | 707R9002 | 707R9003 | 707R9004 | |
| Neu5Ac (mol/ mol) | 15.0 | 17.2 | 16.7 | 16.1 | 17.6 | 16.5 |

(R20: 200 L scale batch for laboratory use, 707R9001~707R9004: GMP 500 L scale batch)

<1-13a> Determination of Sialic Acid Contents (Bio-LC) (2)

Figure 23:
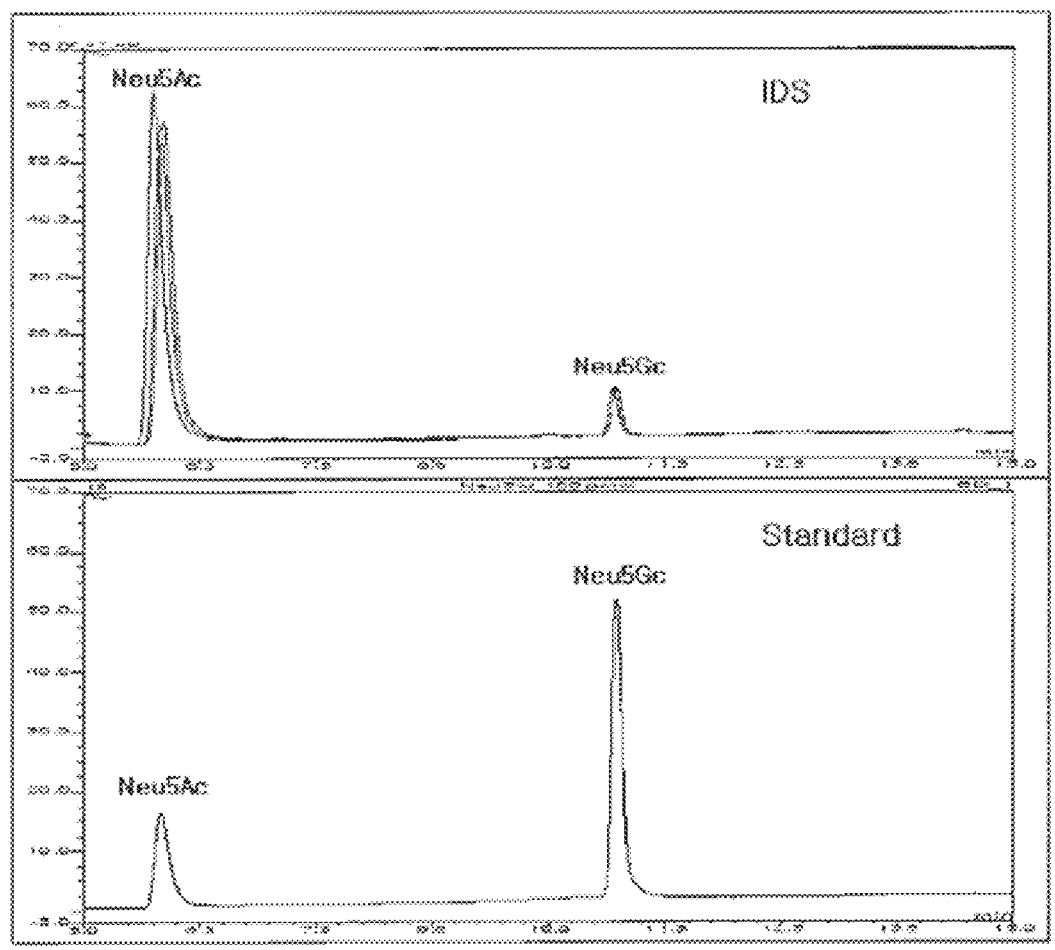
FIG. 23 shows the sialic acid reference and sialic acid composition chromatograms of the IDS.

In the second analysis, IDS was hydrolyzed in 0.1 N hydrochloric acid (HCl), and then the hydrolysate was analyzed using liquid chromatography (High Performance Anion-Exchange Chromatography with Pulsed Amperometric Detection; HPAEC-PAD). The assay was carried out by Protagen AG. A reference sialic acid concentration of which was already known was analyzed under the same conditions, and molar ratios of sialic acid to glycoprotein were obtained by comparison of the areas. Analysis was conducted in triplicate. Sialic acid reference and sialic acid composition chromatograms of the IDS are shown in FIG. 23 and the molar ratios of sialic acid are summarized in Table 7. As shown in the data there are approximately 14.7 moles of sialic acid per mole of IDS, which is similar to the ratio obtained in the first analysis, i.e., 16.5 moles per mole of IDS.

IDS was hydrolyzed with 0.5M HCl and the hydrolysate was analyzed using liquid chromatography (High Performance Anion-Exchange Chromatography with Pulsed Amperometric Detection; HPAEC-PAD). Sialic acid of known concentrations was analyzed under the same condition, and molar ratios of Sialic acid to glycoprotein were obtained by comparison of the areas.

TABLE 7

Analysis results for sialic acid (Bio-LC method)

| Sample | Retention time [min] | Rel. Stand. Dev. | Amount [pmol/10 μl] | Rel. Stand. Dev. | Molar ratio (mol/mol) |
|---|---|---|---|---|---|
| Neu5Ac | 5.82 | 1.03% | 439.16 | 2.95% | 14.68 |
| Neu5Gc | 10.72 | 0.18% | 17.84 | 1.36% | 0.60 |

<1-15> Determination of Oligosaccharide Pattern

Figure 19:
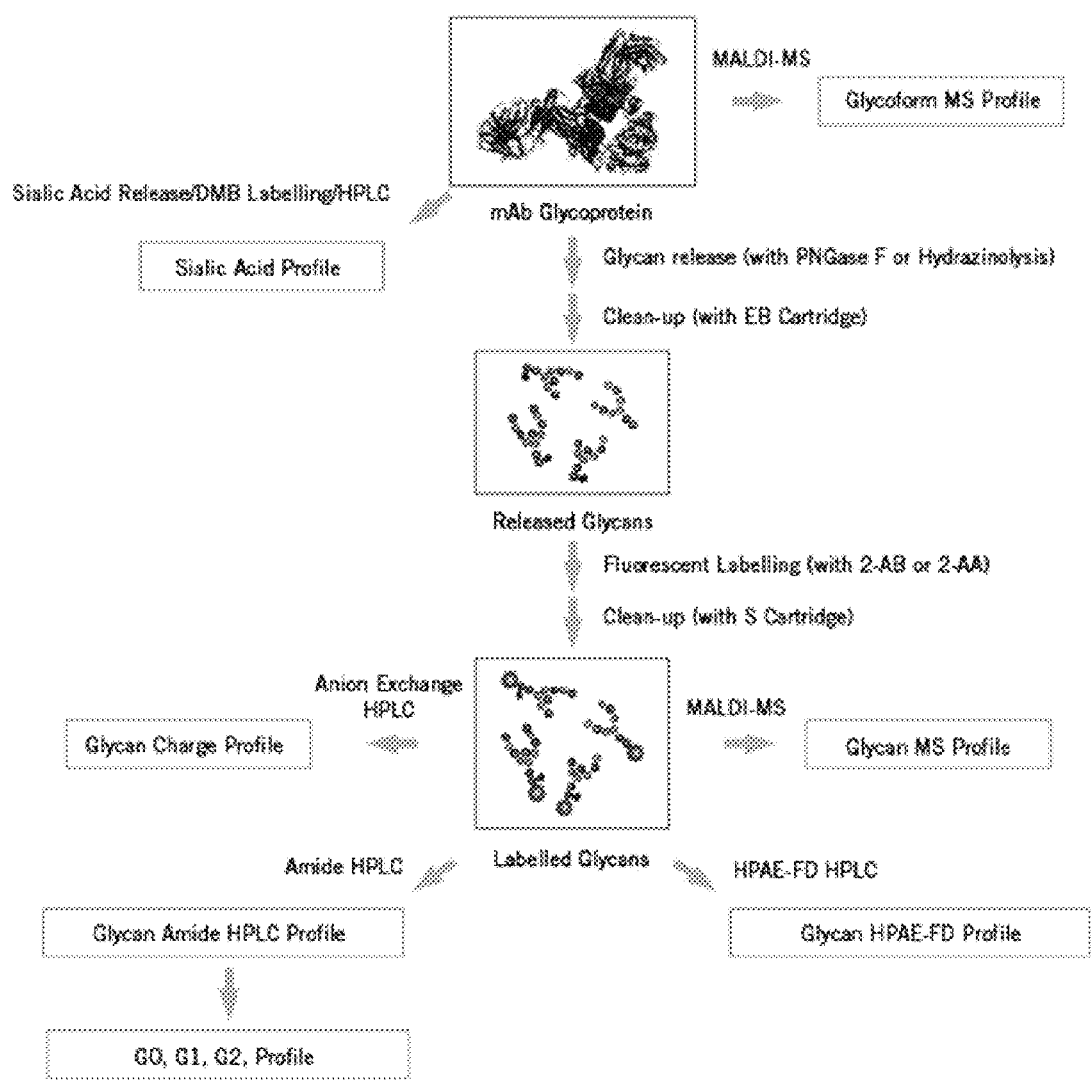
FIG. 19 shows a glycoprofiling scheme for antibody and chemistry of 2-AB labeling.

The oligosaccharide pattern of the sample was determined using IE-HPLC (Ion Exchange-High Performance Liquid Chromatography). In this test, samples are treated with PNGase F to deglycosylate the proteins in the sample, and then the released glycans are labeled 2-AB (2-aminobenzamide). And 2-AB labeled glycans are analyzed by ion exchange HPLC with a fluorescence detector. A glycoprofiling scheme for antibody and chemistry of 2-AB labeling are shown in FIG. 19.

The sample of the IDS composition obtained in Example 1 <1-5> (after affinity chromatography) was diluted to 1 mg/ml using water. 45 ul of 1 mg/ml samples and 5 ul of 10× denaturing buffer were mixed and allowed to stand at 50° C. for about 10 minutes, and 1 uL of PNGase F was added and incubate the mixture at 37° C. for about 6 hours. Glycans are isolated through solid phase extraction and label the isolated glycans with 2-AB dye. Oligosaccharide pattern was determined using GlycoSep C HPLC column (mobile phase A: 200 ml of 100% acetonitrile and 800 ml of filtered water; mobile phase B: 40% acetonitrile (500 ml) and 500 mM ammonium formate (500 ml) were mixed and adjusted to pH 4.5 using formic acid).

Figure 20:
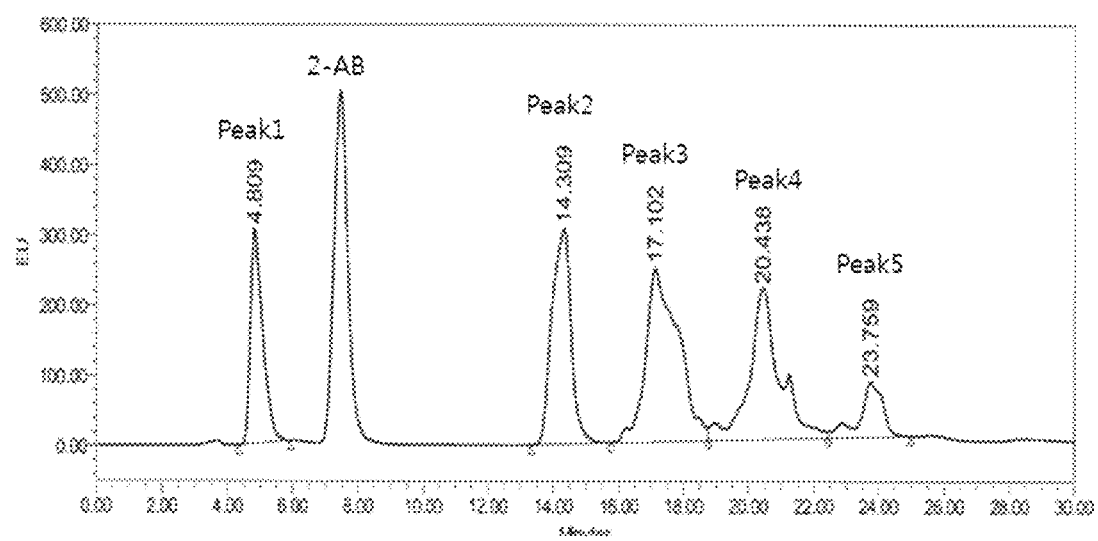
FIG. 20 shows the oligosaccharides pattern of the IDS obtained in Example 1 <1-5>.

The results are shown in FIG. 20. As shown in FIG. 20, the IDS composition obtained in Example 1 meets the oligosaccharide pattern acceptance criteria.

<1-14> Determination of IDS Charge Variance

Proteins migrate to the negative pole when the pH is higher than the isoelectric point (pH and pI at which the total electric charge becomes 0) and to the positive pole when the pH is lower than the isoelectric point. There are two types of ion exchanger used for ion exchange chromatography: cation exchangers and anion exchangers, to each of which counter ions (Na$^+$, Cl$^-$, etc.) are electrostatically bound. Therefore, when the target protein is a basic protein that migrates to the positive pole, it is bound to a cation exchanger with a negative electric charge. When it is an acidic protein that migrates to the negative pole, it is bound to an anion exchanger with a positive electric charge. Bond strength increases according to the size of the total electric charge of the protein. When the ion concentration (salt concentration) of the elution buffer is gradually increased, the bound proteins are eluted in order of weakest to strongest bonds.

In this test, a purity of the IDS obtained in Example 1 <1-5> (after affinity chromatography) and ELAPRASE®, a commercially available therapeutic agent for Hunter syndrome, were measured using Ion Exchange High performance Liquid Chromatography (IE-HPLC). A formulation buffer (as a blank formulation) was prepared, which contains 950 mL of ultrapure distilled water, 0.22 g of polysorbate 20, 2.25 g of sodium phosphate monobasic monohydrate, 0.99 g of sodium phosphate dibasic heptahydrate, and 8 g of sodium chloride, pH 6.0).

The IE-HPCL operation conditions are shown in Table 8 below:

TABLE 8

IE-HPLC Operation Conditions

| Mobile Phase | A: 20 mM Bis-Tris, pH 7.0 |
| | B: 20 mM Bis-Tris + 0.5M sodium chloride, pH 7.0 |
| Column | TOSOH SuperQ-5PW (7.5 × 75 mm, 10 um) |
| Flow Rate | 0.5 mL/min |
| Temperature | Column: 30° C., Sampler: 4° C. |
| Injection Volume | 100 μL |
| Detector | 280 nm |
| Run Time | 70 min |

| Gradient | Time | Flow rate | % A | % B |
|---|---|---|---|---|
| | 0 | 0.5 | 70 | 30 |
| | 10 | 0.5 | 70 | 30 |
| | 45 | 0.5 | 0 | 100 |
| | 50 | 0.5 | 0 | 100 |
| | 55 | 0.5 | 70 | 30 |
| | 70 | 0.5 | 70 | 30 |

Figure 21A:
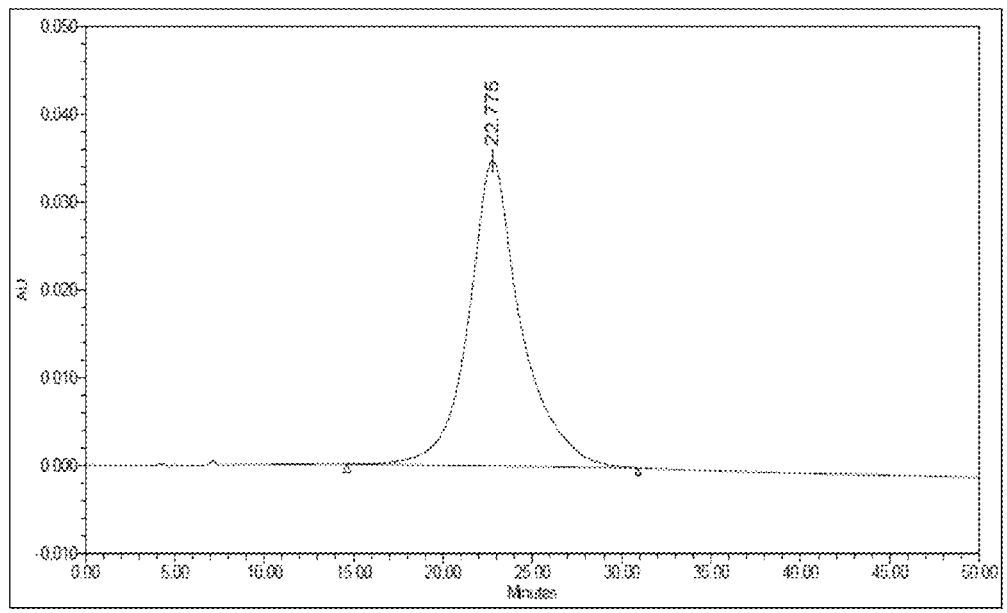
FIGS. 21(A) and 21(B) show the Ion Exchange High Performance Liquid Chromatography results of the IDS obtained in Example 1-5 and the comparative commercially available product, ELAPRASE®, respectively.
Figure 21B:
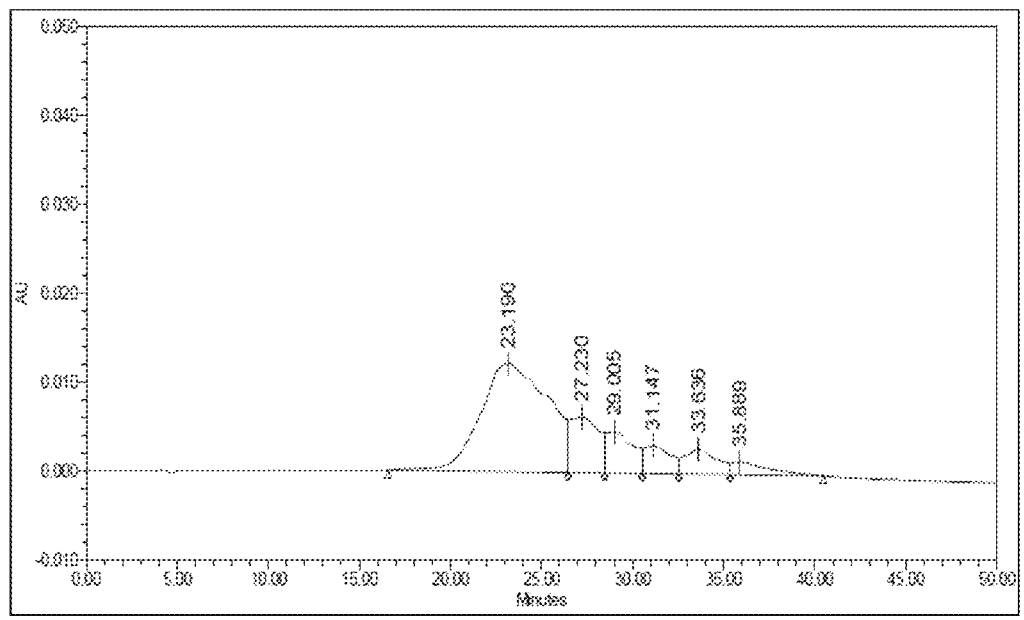

The results are shown in FIGS. 21(A) and 21(B). The results in FIGS. 21(A) and 21(B) show that the IDS obtained by a method according to an embodiment of the invention, which shows a single peak, is surprisingly improved purity compared to ELAPRASE® which show multiple peaks.

<1-14A> Isoelectric Point Analysis

The purpose of this test is to confirm isoelectric point of IDS by using vertical isoelectric focusing technique.

Various amounts of electrical charge carried by proteins can be used to separate proteins based on the charge that they carry when an electrical field is applied. Due to its amphotropic nature, a protein has a net negative charge when the pH is greater than pI, and a protein has a net positive charge when the pH is smaller than pI. Thus, when a strong electrical force is applied to an established pH gradient increasing from anode to cathode, and a protein migrate according to the gradient until the protein reaches the pH region that corresponds to its pI. This assay was conducted to analyze isoelectric point by using a 2D concentration gradient.

Figure 24:
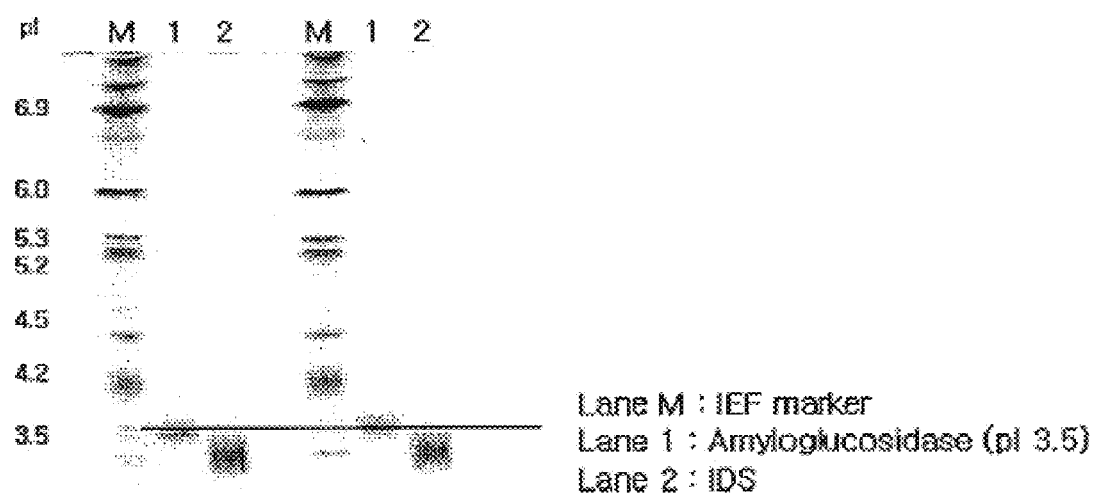
FIG. 24 shows that IDS showed a band within the pH range of 3.5 or lower, as shown by an assay to analyze isoelectric point using a 2D concentration gradient.
Figure 25A:
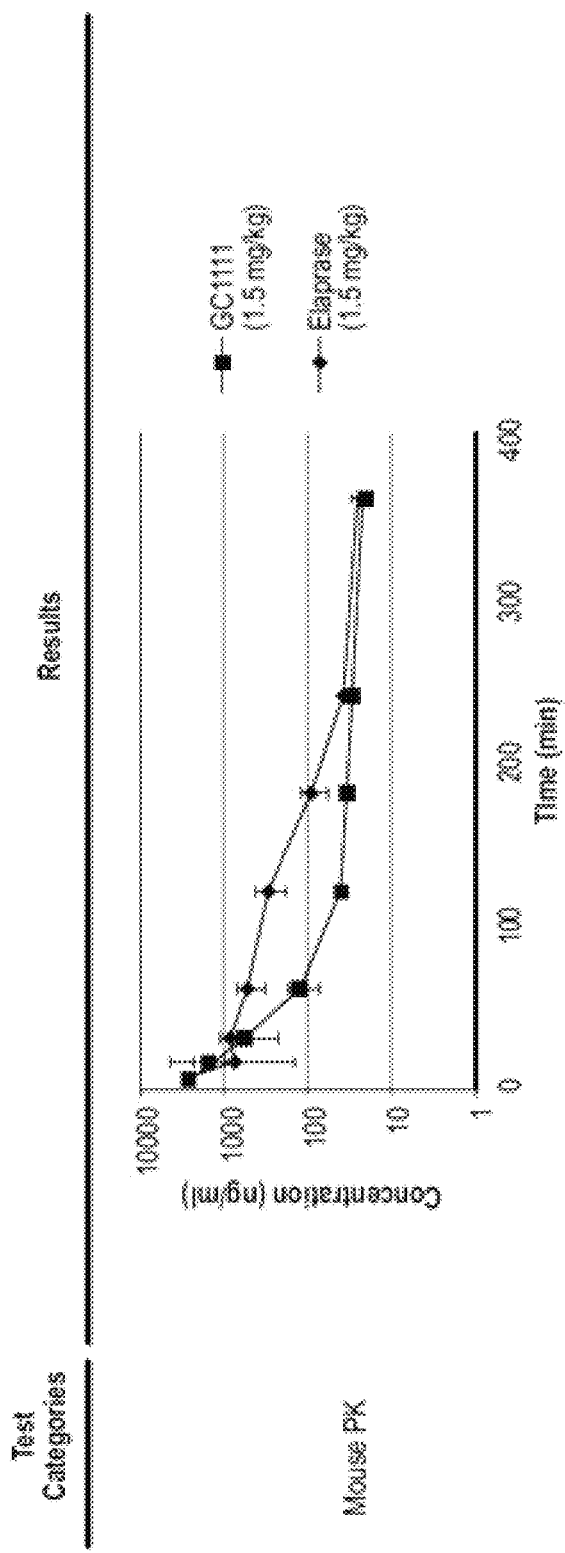
FIG. 25A shows that GC1111 and ELAPRASE® reduced urinary GAG content down to normal mice level in a 24 week efficacy test in an IDS knock-out mouse.
Figure 25F:
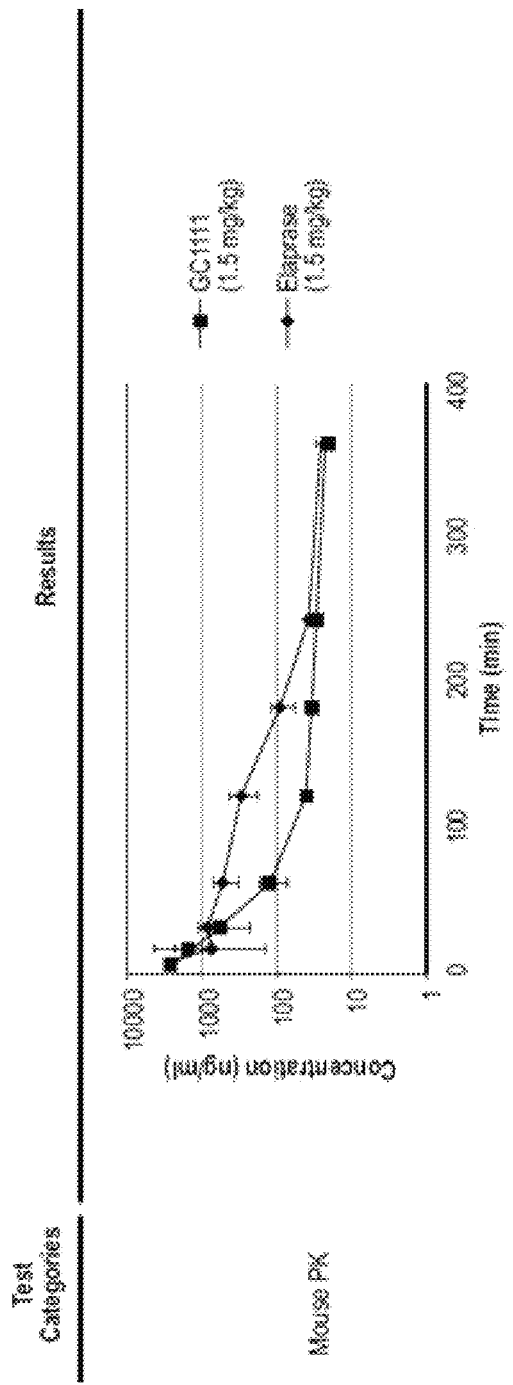
FIG. 25F shows mouse PK data for GC1111 and ELAPRASE®.

As a result, the IDS showed a band within the pH range of 3.5 or lower (FIG. 24).

Experimental Example 2: Clinical Analysis for Effect of IDS

Thirty one patients with Hunter syndrome were divided into three groups, administered with the IDS of the present invention and analyzed for parameters associated with Hunter syndrome. ELAPRASE®, a commercially available therapeutic agent for Hunter syndrome, was used as a positive control.

<2-1> Change in Urine GAG Level (Primary Check Parameter for Validity Test)

The three groups of Hunter syndrome patients were administered for 24 weeks with ELAPRASE® (0.5 mg/kg) and the IDS of the present invention (0.5 mg/kg and 1.0 mg/kg), and urine GAG (Glycosaminoglycan) levels were measured as reported previously (Conn. Tissue Res. Vol. 28, pp 317-324, 1990; Ann. Clin. Biochem. Vol. 31, pp 147-152, 1994). Measurements are summarized in Table 9, below.

TABLE 9

Change in Urine GAG Level with IDS Administration

| Group | ELAPRASE® (0.5 mg/kg) | Inventive IDS (0.5 mg/kg) | Inventive IDS (1.0 mg/kg) |
|---|---|---|---|
| Change in urine GAG level (%) | −18.7 | −29.5 | −41.1 |

In Hunter syndrome patients, as shown in Table 9, urine GAG levels were decreased by 18.7% upon the injection of ELAPRASE®, but by 29.5% upon the injection of the IDS of the present invention at the same dose. In addition, when injected at a dose of 1.0 mg/kg, the IDS of the present invention reduced the urine GAG level by as much as 41.1%. These results demonstrate that the IDS of the present invention is effectively therapeutic for Hunter syndrome, a disease caused as a result of the accumulation of GAG.

<2-2> 6-MWT (6 Minute Walking Test) Change (Secondary Checking Parameter for Validity Test)

After Hunter syndrome patients were administered with ELAPRASE® and the IDS of the present invention for 24 weeks, the distances which they walked for 6 minutes were measured according to the method described in AM. J. Respir. Crit. Care. Med., Vol 166, pp 111-117, 2002. The results are given in Table 10, below.

TABLE 10

6-MWT Test Results

| Group | ELAPRASE® (0.5 mg/kg) | Inventive IDS (0.5 mg/kg) | Inventive IDS (1.0 mg/kg) |
|---|---|---|---|
| 6-MWT Distance (m) | 5.9 | 67.6 | 52.8 |
| 6-MWT Change (%) | 1.3 | 18.2 | 13.4 |

As shown in Table 10, the 6-WMT change was merely 1.3% for the patients administered with ELAPRASE®, but increased to 18.2% for the patients administered with the same dose of the IDS of the present invention. Hunter syndrome patients have trouble walking due to contracture. However, the IDS of the present invention improves the symptoms and thus is effective for the treatment of Hunter syndrome.

<2-3> Efficacy and Toxicity Tests in Mouse Model

Efficacy and toxicity tests of GC1111 of the present invention were conducted using mouse model and the results are summarized in FIG. 25A-FIG. 25F and Table 11. Table 11 shows that GC1111 is taken into the cells faster than ELAPRASE® based on in vitro test results and toxicity test results of GC1111 and ELAPRASE®.

TABLE 11

| Test Item | IV (n = 3) | $C_{max}$ (ng/ml) | $AUC_{last}$ (ng * h/ml) | Terminal $T_{1/2}$ (h) | $MRT_{last}$ (h) |
|---|---|---|---|---|---|
| GC1111 | 1.5 mg/kg | 2478.03 | 1043.73 | 2.47 | 0.78 |
| ELPRASE® | | 3184.67 | 1743.8 | 1.68 | 1.07 |

| | GC1111 uptake into the cell takes place at a faster rate than that of Elaprase based on in vitro test results | |
|---|---|---|
| Toxicity test | GC1111 | ELAPRASE®* |
| Single-dose toxicity in rats | 0/5/10/20 mg/kg | Same as left |
| Single-dose toxicity in monkeys and safety pharmacology | No abnormal clinical signs were observed | Same as left |
| 4 wk repeated toxicity test in monkeys | | Not conducted |
| 26 wk repeated toxicity test in monkeys | 0/0.5/2.5/12.5 mg/kg NOEL: 12.5 mg/kg Histopathologic diagnosis No abnormal clinical signs were observed Immunogenicity diagnosis Some (2 subjects) were test positive after 13 wk 26 All subjects were test negative after 26 wk | 0/0.5/2.5/12.5 mg/kg Histopathologic diagnosis One subject from high-dose group: liver granuloma observed One subject from intermediate-dose group: Some histiocytosis was seen in mesenteric lymph nodes No other abnormal clinical signs were observed Immunogenicity diagnosis Antibodies were formed in 2 out of 4 subjects from 2.5 mg/kg |

TABLE 11-continued

| | | group, and 4 out of 6 subjects from 12.5 mg/kg group, but no effect when drug was exposed in blood |
|---|---|---|
| Reproductive toxicity test in rats | 0/0.5/1.5/5 mg/kg No abnormal clinical signs were observed | Same as left |

*Reference for Elaprase non-clinical studies: FDA BLA (Biologics License Applications)

<2-4> Change in Liver Volume (Secondary Check Parameter for Validity Test): Liver Volume Hunter syndrome patients were administered for 24 weeks with ELAPRASE® and GC1111, and their liver volume was measured by liver ultrasonography, and the results were evaluated by comparing with baseline values.

*Hepatomegaly was observed in Hunter syndrome patients due to accumulation of GAG. The results are shown in Table 12.

TABLE 12

| Group | ELAPRASE®_0.5 mg/kg | GC1111_0.5 mg/kg | GC1111_1.0 mg/kg |
|---|---|---|---|
| Change in liver volume(vol, cc) | −258 | −110 | −195.5 |
| Change in liver volume(rate, %) | −14.6 | −6.2 | −8.5 |

<2-5> Change in Urine GAG Level (Secondary Check Parameter for Validity Test)

Hunter syndrome patients were administered for 24 weeks with ELAPRASE® and GC111, and their urine GAG levels were measured, and evaluated by comparing with baseline values.

*Urinary GAG was detected from Hunter syndrome patients because degradation of GAG did not take place due to iduronate-2-sulfatase deficiency. The results are shown in Table 13.

TABLE 13

| Group | ELAPRASE® 0.5 mg/kg | GC1111_0.5 mg/kg | GC1111_1.0 mg/kg |
|---|---|---|---|
| Change in urine GAG(mg GAG/g Creatinine) | −23.8 | −49.6 | −50.2 |

<2-6> Change in LV End Diastolic, Systolic Volume (Secondary Check Parameter for Validity Test): Contraction and Relaxation of Heart Hunter syndrome patients were administered with ELAPRASE® and GC 1111 for 24 weeks, and LV end diastolic and systolic volumes were measured by using echocardiography, and the results were evaluated by comparing with baseline values.

*Cardiomegalia was observed in Hunter syndrome patients. Increased diastolic volume and decreased systolic volume indicate an improved myocardial contractility. The results are shown in Table 14.

TABLE 14

| Group | ELAPRASE®_0.5 mg/kg | GC1111_0.5 mg/kg | GC1111 1.0 mg/kg |
|---|---|---|---|
| Change in LV end diastolic volume (vol, cc) | 0.6 | 5.8 | 5 |
| Change in LV end diastolic volume (rate, %) | 1.7 | 9.1 | 6.9 |
| Change in LV end systolic volume (vol, cc) | −3.3 | −1.2 | 3.2 |
| Change in LV end systolic volume (rate, %) | −17.2 | −5.7 | 10.8 |

<2-7> Change in LV Mass Index (Secondary Check Parameter for Validity Test): Hypertrophic Myocytes Hunter syndrome patients were administered for 24 weeks with ELAPRASE® and GC1111, and LV mass indices were measured by using echocardiography, and the results were evaluated by comparing with baseline values.

*The degree of hypertrophic myocytes was analyzed by using LV mass index. The results are shown in Table 15.

TABLE 15

| Group | ELAPRASE®_0.5 mg/kg | GC1111_0.5 mg/kg | GC1111_1.0 mg/kg |
|---|---|---|---|
| Change in LV mass index $(g/m^{2.7})$ | −0.9 | −1.9 | −0.6 |
| Change in LV mass index (%) | −1.7 | −2.9 | −0.6 |

<2-8> Change in LV Ejection Fraction (Secondary Check Parameter for Validity Test): Cardiac Function Hunter syndrome patients were administered for 24 weeks with ELAPRASE® and GC1111, and their LV ejection fractions were measured by echocardiography, and the results were evaluated by comparing with baseline values. The results are shown in Table 16.

TABLE 16

| Group | ELAPRASE®_0.5 mg/kg | GC1111_0.5 mg/kg | GC1111_1.0 mg/kg |
|---|---|---|---|
| Change in LV ejection fraction (%) | 1.5 | 3.6 | −0.6 |
| Change in LV ejection fraction (%) | 2 | 5 | −1 |

<2-9> Change in Absolute FVC (Secondary Check Parameter for Validity Test): Pulmonary Function During Respiration After Hunter syndrome patients were administered with ELAPRASE® and GC1111 for 24 weeks, absolute FVC was measured by using pulmonary function test, and the results were evaluated by comparing with base line values.

*Hunter syndrome patients experience narrowed respiratory tract due to GAG accumulation in respiratory tract; in severe cases, respiratory obstruction occurs and tracheotomy must be performed. The results are shown in Table 17.

TABLE 17

| Group | Elprase ®_0.5 mg/kg | GC1111_0.5 mg/kg | GC1111_1.0 mg/kg |
|---|---|---|---|
| Change in absolute FVC (L) | 0 | 0.1 | 0.2 |
| Change in absolute FVC (%) | 0 | 12.6 | 17 |

<2-10> Safety Evaluation

1) Adverse Drug Reaction (ADR)

In Elaprase®_0.5 mg/kg group, 2 of 11 subjects experienced a total of 19 adverse drug reactions.

In GC1111_0.5 mg/kg group, 1 of 10 subjects experienced a total of 4 adverse drug reactions.

In GC1111_1.0 mg/kg group, 2 of 10 subjects experienced a total of 3 adverse drug reactions.

*All the adverse drug reactions observed were mild symptoms as expected, and these ADRs were controllable by discontinuation of drug at lower and less frequent dosing regimens.

2) Immunogenicity

Three groups of Hunter syndrome patients were administered with GCIII for 24 weeks and immunogenicity test was performed. As a result, no changes were observed in the status on prevalence of GC1111 antibodies and neutralizing antibodies in Hunter syndrome patients before and after the administration.

What is claimed is:

1. A method for preparing a composition comprising an iduronate-2-sulfatase (IDS) having the amino acid sequence of SEQ ID NO: 1, wherein a molar ratio of the IDS of which amino acid at position 59 in the SEQ ID NO: 1 is formylglycine (FGly) is 65% or higher of the total amount of the IDS in the composition, said method comprising:
   (a) subjecting a culture of a host cell to an anion exchange chromatography, wherein the host cell is transfected with a gene encoding an IDS of SEQ ID NO: 1 and the culture contains the IDS, comprising eluting the IDS with a first elution buffer of pH 5.5-7.5;
   (b) subjecting the eluant obtained in (a) to a hydrophobic chromatography, comprising eluting the IDS with a second elution buffer of pH 5.0-7.0; and
   (c) subjecting the eluant obtained in (b) to a cation exchange chromatography, comprising eluting the IDS with a third elution buffer of pH 4.0-6.0 to obtain the composition.

2. The method of claim 1, wherein the host cell is a Chinese hamster ovary cell.

3. The method of claim 1, wherein the IDS is a recombinant human IDS.

4. The method of claim 1, further comprising a step of lowering pH of the eluant obtained in step (b) to a range of pH 3.0-4.0.

5. The method of claim 1, further comprising
   (d) subjecting the eluant obtained in (c) to an affinity chromatography, comprising eluting the IDS using a fourth elution buffer of pH 6.0-8.0.

6. The method of claim 1, wherein the first elution buffer comprises sodium chloride.

7. The method of claim 1, wherein the second elution buffer contains glycerol.

8. The method of claim 1, wherein the third elution buffer contains glycerol.

9. The method of claim 1, wherein the composition comprising the IDS has a host cell derived DNA content of 0.1 ng/mg or less based on the total amount of the composition.

10. The method of claim 1, wherein the composition comprising the IDS has a host cell derived protein content of 20 ng/mg or less based on the total amount of the composition.

11. The method of claim 1, wherein the composition comprising the IDS has an isoelectric point of 3.5 or less.

12. The method of claim 1, wherein the molar ratio of the IDS of which amino acid at position 59 in the SEQ ID NO: 1 is FGly is 75% or higher of the total amount of the IDS in the composition.

13. The method of claim 1, wherein a purity of the IDS in the composition is 98% or higher, determined by SE-HPLC.

14. A composition comprising a purified recombinant human iduronate-2-sulfatase (IDS) having the amino acid sequence of SEQ ID NO: 1, wherein a molar ratio of the IDS in which the amino acid residue at position 59 in the IDS amino acid sequence is formylglycine (FGly) is 65% or higher, and wherein the composition contains 20 ng/mg or less of host cell derived proteins, based on the total amount of the composition.

15. The composition of claim 14, wherein the molar ratio of the IDS in which the amino acid residue at position 59 is FGly is 75% or higher.

16. The composition of claim 14, which has an isoelectric point of 3.5 or less.

17. A method for producing a formulation comprising an iduronate-2-sulfatase (IDS) having the amino acid sequence of SEQ ID NO: 1, wherein a molar ratio of the IDS of which amino acid at position 59 in the SEQ ID NO: 1 is formylglycine (FGly) is 65% or higher of the total amount of the IDS in the composition, said method comprising:
   (a) subjecting a culture of a host cell to an anion exchange chromatography, wherein the host cell is transfected with a gene encoding an IDS of SEQ ID NO: 1 and the culture contains the IDS, comprising eluting the IDS with a first elution buffer of pH 5.5-7.5;
   (b) subjecting the eluant obtained in (a) to a hydrophobic chromatography, comprising eluting the IDS with a second elution buffer of pH 5.0-7.0; and
   (c) subjecting the eluant obtained in (b) to a cation exchange chromatography, comprising eluting the IDS with a third elution buffer of pH 4.0-6.0 to obtain a purified IDS; and
   (d) combining the purified IDS with a pharmaceutically acceptable carrier to obtain the formulation.

18. The method of claim 17, wherein the pharmaceutically acceptable carrier is a buffer comprising a distilled water, polysorbate 20, sodium phosphate monobasic monohydrate, sodium phosphate dibasic heptahydrate, and sodium chloride.

19. The method of claim 17, wherein the formulation further comprises a buffer containing a distilled water, polysorbate 20, sodium phosphate monobasic monohydrate, sodium phosphate dibasic heptahydrate, and sodium chloride.

20. The method of claim 1, wherein the first elution buffer in step (a) has a pH of 7.0±0.3.

21. The method of claim 1, wherein the second elution buffer in step (b) has a pH of 5.5±0.2.

22. The method of claim 1, wherein the third elution buffer in step (c) has a pH of 5.3±0.2.

23. The method of claim 3, wherein the pH of the eluant obtained in step (b) is lowered to 3.7±0.05.

24. The method of claim 4, wherein the fourth elution buffer has a pH of 6.2±0.2.

25. The method of claim 17, wherein the first elution buffer in step (a) has a pH of 7.0±0.3.

26. The method of claim 17, wherein the second elution buffer in step (b) has a pH of 5.5±0.2.

27. The method of claim 17, wherein the third elution buffer in step (c) has a pH of 5.3±0.2.

\* \* \* \* \*

SEQUENCE LISTING

```
<160> NUMBER OF SEQ ID NOS: 9

<210> SEQ ID NO 1
<211> LENGTH: 525
<212> TYPE: PRT
<213> ORGANISM: Unknown
<220> FEATURE:
<223> OTHER INFORMATION: Synthetic construct of IDS protein

<400> SEQUENCE: 1

Ser Glu Thr Gln Ala Asn Ser Thr Thr Asp Ala Leu Asn Val Leu Leu
  1               5                  10                  15

Ile Ile Val Asp Asp Leu Arg Pro Ser Leu Gly Cys Tyr Gly Asp Lys
                 20                  25                  30

Leu Val Arg Ser Pro Asn Ile Asp Gln Leu Ala Ser His Ser Leu Leu
             35                  40                  45

Phe Gln Asn Ala Phe Ala Gln Gln Ala Val Cys Ala Pro Ser Arg Val
     50                  55                  60

Ser Phe Leu Thr Gly Arg Arg Pro Asp Thr Thr Arg Leu Tyr Asp Phe
 65                  70                  75                  80

Asn Ser Tyr Trp Arg Val His Ala Gly Asn Phe Ser Thr Ile Pro Gln
                 85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125

Ser Phe Pro Pro Tyr His Pro Ser Ser Glu Lys Tyr Glu Asn Thr Lys
130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
```

```
            210                 215                 220
Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
    290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
        355                 360                 365

Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
        435                 440                 445

Gln Trp Asn Ser Asp Lys Pro Ser Leu Lys Asp Ile Lys Ile Met Gly
    450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro
        515                 520                 525

<210> SEQ ID NO 2
<211> LENGTH: 48
<212> TYPE: DNA
<213> ORGANISM: Artificial Sequence
<220> FEATURE:
<223> OTHER INFORMATION: IDS 1 forward primer

<400> SEQUENCE: 2
ctatgggtat ctggtacctg tgggatgccg ccacccccgga ccggccga        48

<210> SEQ ID NO 3
<211> LENGTH: 73
<212> TYPE: DNA
<213> ORGANISM: Artificial Sequence
<220> FEATURE:
<223> OTHER INFORMATION: IDS 2 forward primer
```

<400> SEQUENCE: 3
tgcagatatc cggagcaaga tggattcaca ggcccaggtt cttatgttac tgctgctatg    60
ggtatctggt acc                                                      73

<210> SEQ ID NO 4
<211> LENGTH: 28
<212> TYPE: DNA
<213> ORGANISM: Artificial Sequence
<220> FEATURE:
<223> OTHER INFORMATION: IDS 3 reverse primer

<400> SEQUENCE: 4 gggcccctcaa ggcatcaaca actggaaa                                     28

<210> SEQ ID NO 5
<211> LENGTH: 48
<212> TYPE: DNA
<213> ORGANISM: Artificial Sequence
<220> FEATURE:
<223> OTHER INFORMATION: IDS N1 forward primer

<400> SEQUENCE: 5
cagcaagcag gtcattgttc caacatgccg ccaccccgga ccggccga                48

<210> SEQ ID NO 6
<211> LENGTH: 49
<212> TYPE: DNA
<213> ORGANISM: Artificial Sequence
<220> FEATURE:
<223> OTHER INFORMATION: IDS N2 forward primer

<400> SEQUENCE: 6
tgcagatatc ccagctacag tcggaaacca tcagcaagca ggtcattgt               49

<210> SEQ ID NO 7
<211> LENGTH: 24
<212> TYPE: DNA
<213> ORGANISM: Artificial Sequence
<220> FEATURE:
<223> OTHER INFORMATION: IDS 4 reverse primer

<400> SEQUENCE: 7
gaagatatcc cagggtgaaa gact                                          24

<210> SEQ ID NO 8
<211> LENGTH: 20
<212> TYPE: DNA
<213> ORGANISM: Artificial Sequence
<220> FEATURE:
<223> OTHER INFORMATION: T7 forward primer

<400> SEQUENCE: 8
aatacgactc actataggga                                               20

<210> SEQ ID NO 9
<211> LENGTH: 525
<212> TYPE: PRT
<213> ORGANISM: Unknown
<220> FEATURE:
<223> OTHER INFORMATION: Synthetic construct of IDS peptide variant
<220> FEATURE:
<221> NAME/KEY: MOD_RES
<222> LOCATION: (59)..(59)
<223> OTHER INFORMATION: Xaa = formylglycine

<400> SEQUENCE: 9

```
Ser Glu Thr Gln Ala Asn Ser Thr Thr Asp Ala Leu Asn Val Leu Leu
  1               5                  10                  15

Ile Ile Val Asp Asp Leu Arg Pro Ser Leu Gly Cys Tyr Gly Asp Lys
             20                  25                  30

Leu Val Arg Ser Pro Asn Ile Asp Gln Leu Ala Ser His Ser Leu Leu
         35                  40                  45

Phe Gln Asn Ala Phe Ala Gln Gln Ala Val Xaa Ala Pro Ser Arg Val
     50                  55                  60

Ser Phe Leu Thr Gly Arg Arg Pro Asp Thr Thr Arg Leu Tyr Asp Phe
 65                  70                  75                  80

Asn Ser Tyr Trp Arg Val His Ala Gly Asn Phe Ser Thr Ile Pro Gln
                 85                  90                  95

Tyr Phe Lys Glu Asn Gly Tyr Val Thr Met Ser Val Gly Lys Val Phe
                100                 105                 110

His Pro Gly Ile Ser Ser Asn His Thr Asp Asp Ser Pro Tyr Ser Trp
             115                 120                 125

Ser Phe Pro Pro Tyr His Pro Ser Ser Glu Lys Tyr Glu Asn Thr Lys
130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
                180                 185                 190

Pro Phe Phe Leu Ala Val Gly Tyr His Lys Pro His Ile Pro Phe Arg
            195                 200                 205

Tyr Pro Lys Glu Phe Gln Lys Leu Tyr Pro Leu Glu Asn Ile Thr Leu
210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
        355                 360                 365

Gly Arg Gln Ser Met Asp Leu Val Glu Leu Val Ser Leu Phe Pro Thr
370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415
```

-continued

```
Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
        435                 440                 445

Gln Trp Asn Ser Asp Lys Pro Ser Leu Lys Asp Ile Lys Ile Met Gly
    450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro
        515                 520                 525
```